United States Patent
Kobaru et al.

(10) Patent No.: US 6,667,483 B2
(45) Date of Patent: Dec. 23, 2003

(54) APPARATUS USING CHARGED PARTICLE BEAM

(75) Inventors: Atsushi Kobaru, Hitachinaka (JP); Tadashi Otaka, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 397 days.

(21) Appl. No.: 09/842,789

(22) Filed: Apr. 27, 2001

(65) Prior Publication Data

US 2001/0050343 A1 Dec. 13, 2001

(30) Foreign Application Priority Data

May 12, 2000 (JP) ........................................ 2000-140738

(51) Int. Cl.⁷ ............................................... H01J 37/26
(52) U.S. Cl. ............................. 250/492.2; 250/492.3; 250/492.22; 250/310; 250/398; 250/396 R
(58) Field of Search ....................... 250/492.2, 492.22, 250/492.3, 310, 398, 396 R

(56) References Cited

U.S. PATENT DOCUMENTS

| | | |
|---|---|---|
| 4,814,682 A | 3/1989 | Yamada |
| 5,384,463 A | * 1/1995 | Honjo et al. ................ 250/398 |
| 5,894,056 A | * 4/1999 | Kakizaki et al. ............... 430/5 |

FOREIGN PATENT DOCUMENTS

| | | |
|---|---|---|
| JP | 3-175507 | 7/1991 |
| JP | 8-297508 | 11/1996 |

* cited by examiner

*Primary Examiner*—Nikita Wells
(74) *Attorney, Agent, or Firm*—Dickstein, Shapiro Morin & Oshinsky LLP

(57) ABSTRACT

An apparatus using charged particle beam is provided with means for detecting positional difference between a target position on a chip pattern within an observation visual field of a microscope after displacing a sample stage thereof and a predetermined position within the visual field, means for storing the detection result and means for determining a new displacement target position for displacement to the predetermined position in subsequent observation while taking into account of the positional difference stored previously and the displacement target position used at the time of storage. When observing another wafer on which the same patterns with the same alignment as the previous one are printed or another pattern on the same wafer, the previous sample stage displacement target designation position is also modified while taking into account of the previous observation visual field position deviation which is registered to the corresponding observation position, and the stage is displaced according to the designation position. Thereby, quick and correct displacement of the observation position within an observation visual field can be realized.

18 Claims, 27 Drawing Sheets

PCJ: EFFECTIVE DATA POINT NUMBER FOR
POSITIONAL DEVIATION CORRECTION

CONDITION: j=pcj

PCJ: EFFECTIVE DATA POINT NUMBER FOR POSITIONAL DEVIATION CORRECTION

PCJ:EFFECTIVE DATA POINT NUMBER FOR
POSITIONAL DEVIATION CORRECTION
CONDITION TERM:i=pcj

READ STATE FROM MEMORY UNIT ON DEVICE B

PCJ:EFFECTIVE DATA POINT NUMBER FOR
POSITIONAL DEVIATION CORRECTION
CONDITION TERM:i=pcj

WRITE STATE TO MEMORY UNIT ON DEVICE B

DEVICE A

DEVICE B

PCJ:EFFECTIVE DATA POINT NUMBER FOR
POSITIONAL DEVIATION CORRECTION
CONDITION TERM:i=pcj

READ STATE FROM MEMORY UNIT ON DEVICE B

PCJ:EFFECTIVE DATA POINT NUMBER FOR
    POSITIONAL DEVIATION CORRECTION
CONDITION TERM:i=pcj

WRITE STATE IN MEMORY UNIT ON DEVICE B

APPARATUS USING CHARGED PARTICLE BEAM

BACKGROUND OF THE INVENTION

The present invention relates to an apparatus using charged particle beam with a sample stage drive device on which a sample to be measured including observation thereof is mounted, and, in particular, relates to an apparatus using charged particle beam such as a scanning type electron microscope which is suitable for automatic observation of a sample with such as a scanning type electron microscope and an optical type microscope, of which configuration, internal structure or location is known in advance.

CONVENTIONAL ART

It is already known a few methods in which when observing with a scanning type electron microscope a sample of which configuration, internal structure or location is known in advance, drawings or photographs showing the same and coordinate used for designating position of observation portion in the sample are related with displacement of a sample stage with some proper measure and a portion on the sample desired to be observed is quickly and automatically displaced in a simple manner into a visual field. Among these methods a method, for example, disclosed in U.S. Pat. No. 4,814,682 is one of effective ones. The disclosed method is intended to reduce workload for observation by manually designating position of a portion desired of observation, however, in a current scanning type electron microscope the disclosed method is further advanced and an automatic designation through a computer is performed. Currently, the method is used for the purpose of observing a microscopic pattern desired to be observed existing in a chip which can not discriminate and recognize on a chip design sheet while assuming respective chips, which are formed in a plurality of pieces on a common supporting body called as a wafer with a same design pattern and with a geometrical location relationship with a predetermined accuracy, as respective samples.

After once mounting actually a wafer on a sample stage, the position where the wafer is fixed temporarily on the sample stage at this instance is assumed as a reference position for observation position designating coordinate on the wafer. A control device for the scanning type electron microscope virtually registers the plurality of chips in a grid shape on the wafer according to the coordinate at this instance while framing such as the chip size, location and rotation direction in the wafer plane in a square chip outer configuration in a relationship based on the chip design data. By making use of the grid coordinate values of observation pattern, portions within a chip are thereafter determined.

Under a condition where a sample is actually mounted on a sample stage, the sample stage is displaced manually while observing the sample with the scanning type electron microscope and the position of a portion designed to be observed is manually designated in advance on the actual sample. The control device for the scanning type electron microscope determines the position of the portion desired to be observed after converting the same into a coordinate value within the chip from the coordinate value of the sample stage at the moment and the chip alignment, and stores the same together with the scanning type electron microscope image of the observed portion while relating thereto. Thereby, for the subsequent observation the control device for the scanning type electron microscope determines a coordinate value of a position to which the sample stage is to be automatically displaced from the coordinate value within the chip of the position for the observation portion and the chip alignment position registered in advance, and further performs an automatic identification of the observation portion through a picture image collation with the image of the observation portion which is stored while relating to the observation portion.

In the above U.S. Pat. No. 4,841,682, before performing an observation with respect to two portions on the actual sample among any portions showing characteristic sample structures the positions based on the design data on the drawing sheet and the position on the actual sample are related, thereby coordinate calibration is performed between the sample stage coordinate and the coordinate on the sample drawing sheet, in that the coordinate used by a coordinate designation means. As a result, when a position of a observation portion is designated by the coordinate designation means thereafter, the observation position can be brought into a visual field with a predetermined accuracy. In particular, when samples which permit designation of an observation position on a same design sheet are mounted on the same supporting body (for example, IC patterns arranged on a sample stage for a pattern comparison), through a provision of a switching function by a sample selection switch, the designation of observation positions of plural samples can be enabled by the same drawing sheet.

In the above U.S. Pat. No. 4,814,682, a sample (IC pattern) arranged on a common supporting body (sample stage) was an object for observation, however, in a recent scanning type electron microscope used for semiconductor manufacturing processes the object for observation is being replaced to a combination of IC patterns arranged on a wafer. Herein, the designation of two characteristic points is not limited on the same sample (the same chip), but is permitted over a plurality of samples (a plurality of chips). Therefore, coordinate on the coordinate designation means which can cover the entire samples located is set and then coordinate calibration between the coordinate on the coordinate designation means and the sample stage coordinate is performed. In such instance, since the plurality of samples (the plurality of chips) are located geometrically on a common supporting body (a wafer) with a predetermined accuracy, an observation position (x, y) can be determined from chip alignment pitch (px, py), chip location (nx, ny) and in-chip position (xd, yd) according to the following equation (1);

$$\left. \begin{array}{l} x = px \times nx + xd \\ y = py \times ny + yd \end{array} \right\} \quad (1)$$

In this method, as a preparation before observation, registration of two portions having characteristic structures is performed. Namely, with reference to the mounted position of the wafer on the sample stage at this moment a two dimensional coordinate designed by two characteristic portions on the mounted wafer is prepared as designated coordinate on the coordinate designation means. On this coordinate a drawing used in the coordinate designation means is prepared from an arrangement of a grid representing such as a chip size and chip location which are defined according to the design data. When observing in subsequent observations another wafer locating totally identical samples (chips) and being mounted on the sample stage, the position for the observation portion on the sample stage is designated based on the above designation coordination. However, the mounting position of a wafer on the sample stage is determined by mechanical contact between the sample stage and the wafer, therefore, a small amount of deviation is caused from the instance when registering the two characteristic portions previously, and the deviation amount varies every observation. In order to correct such deviation, the positions of the two same characteristic points located at the same positions as those registered previously are compared with the positions registered first to thereby perform coordinate calibration. Thus, coordinate calibration between the coordination at the time of registration giving the coordination of the coordinate designation means and the sample stage coordination at the time of observation is performed. Further, the coordination calibration performed by correspondence between two points within the sample in U.S. Pat. No. 4,814,682 was applied to the coordinate representing a geometric location of a plurality of samples (chips) on a common supporting body (wafer) as well as to the coordinate representing the positions of observation portions within a sample (chip) as it is.

However, actually, in a course of printing chips (individual samples) on a wafer (a supporting body), in particular, during semiconductor manufacturing processes, a main factor which determines a positional accuracy of chip alignment on a wafer depends on a positional accuracy of the sample stage in a printing device (hereinafter called as a stepper), on the other hand, a main factor which determines a positional accuracy of observation portions within a chip depends on distortion of a stepper lens. Further, when designating the chip alignment by a single point in the respective chips, a deviation of the sample stage coordinations with in-plane rotation direction of a plane coordinate of respective entire chips causes a same effect when the positions of the observation portions within a chip are deviated. In particular, when observing a portion different from the portion which was used for the coordinate calibration, the deviation will be increased as the distance from the coordinate calibration position increases due to the entire chip rotation, which shows that only with the measure of the coordinate calibration with respect to the coordinate for the set of the coordinate designation means, it is impossible to bring about a visual field of an observation position by the coordinate designation with a sufficiently high positional accuracy, because of the different factors determining the positional accuracy of the both. However, such positional deviation at the time of bringing about a visual field frequently shows a certain tendency with regard to deviation direction and amount, when such visual field bringing about operation by the sample stage displacement is performed several times at the sample positions. Namely, it frequently happens that stop positions for actual visual field collectively appear around a position spaced apart some from a target position in a certain direction, which shows a state representing "a low positional accuracy but a good positional reproducibility".

Further, on the other hand, when displacing a sample stage for respective observation devices, it is frequently caused respective positional deviations inherent to the individual observation devices. For example, FIGS. 17 and 18 show respective examples of positional accuracy of the sample stage for devices A and B. The drawings show loci of actual stage displacement which are determined by measuring respective crossing points on the grids, when the stages are displaced along a straight line on the two dimensional plane. When comparing the both devices, the positional deviations at respective crossing points with respect to respective target positions are not the same in connection with both direction and amount thereof. Further, it is observed even with the same device the deviations are different depending on the target positions.

Although these deviations depend on a direct operation performance of such as a direct operation guide constituting such stages, it is difficult to produce a guide which performs a complete direct operation. Therefore, when displacing a visual field of a microscope through displacement of such stage, and if it is intended to locate a target position on a sample at the center of the visual field, a positional deviation from the center of visual field is inherently caused.

However, such positional deviation at the time of bringing about a visual field frequently shows a certain tendency with regard to deviation direction and amount, when such visual field bringing about operation by the sample stage displacement is performed several times at the sample positions. Namely, it frequently happens that stop positions for actual visual field collectively appear around a position spaced apart some from a target position in a certain direction, which shows a state representing "a low positional accuracy but a good positional reproducibility".

Among two factors of the positional deviations, one caused by the sample and the other caused by the sample stage of a microscope, when one or two are caused at the same time, the positional deviation at the time of bringing about a visual field can be caused. However, regardless that the positional deviation may be caused by either or both of the factors, it will be understood that the state representing "a low positional accuracy but a good positional reproducibility" is obtained.

Until now, in order to correct such positional deviation, several methods of coordinate calibration between the designation coordinate of an observation position and the stage coordinate serving as a reference at the actual displacement have been proposed.

One of the examples is that instead of displacing the stage with reference to the dotted lines in FIG. 17 or FIG. 18, when designating an actual displacement to the stage, the displacement distance is determined with reference to the solid lines to provide the designation value. Since the solid lines show a manner that which the stage is actually displaced, displacements near the crossing points at respective grids show respective effects of certain extent. However, positions remote from these crossing points, for example, any points near the position of the center of gravity are spaced apart from all of the calibration points, therefore, in actual sense a correct calibration is not necessarily performed for the positions. In this instance, if the sides of grids are infinitely reduced, the number of the calibration points increases and the distance therebetween shortened. Therefore, the distance to calibration points from any points are reduced, thereby, the above referred to problem is resolved to a certain extent. However, when increasing the grid points, in that the calibration points, it is necessary to perform many registrations depending on number of the calibration points and when in view of the calibration work which has to be performed by an operator, an increasing of the grid point number has to be limited.

Such phenomenon was actually confirmed that when the visual field is brought about in a scanning type electron microscope with the conventional method, the amount of visual field deviation increases as the observation position is away from the two characteristic points used for the coordinate calibration.

Until now, when such deviation amount is large, in order to cope with such circumstance an image magnification rate of a scanning type electron microscope image is reduced to ensure a broad search area when performing a positional search by means of a picture image collation by making use of a scanning type electron microscope image of the observation portion. However, with this measure it is necessary to perform the picture image collation for all of many objects appearing in the broad area which requires long search time. Further, as one of inherent characteristics of a scanning type electron microscope, when performing an image observation with a low magnification rate, it is likely affected of an image disturbance due to such as charge-up caused by primary electron irradiation, and the scanning type electron microscope image is likely unstabilized which causes a problem of frequent erroneous searches due to erroneous recognition.

Since the magnification for the observation of a scanning type electron microscope which is used these days in a semiconductor manufacturing processes for observation use is high, it is necessary to displace the sample stage with a high positional designation accuracy, in order to bring about an observation object into a visual field. On the other hand, the scanning type electron microscope is required to be operated in a high operation efficiency as well as to perform a process management through an automatic observation.

SUMMARY OF THE INVENTION

The present invention is achieved in view of the conventional problems, and an object of the present invention is to provide an apparatus using charged particle beam such as a scanning type electron microscope which is used for observing faulty chip patterns, in particular, during semiconductor manufacturing processes and which permits quick and accurate displacement of an observation position into an observation visual field.

An apparatus using charged particle beam according to the present invention is provided with means for detecting positional difference between a target position on a chip pattern within an observation visual field of a microscope after displacing a sample stage thereof and a predetermined position within the visual field, means for storing the detection result and means for determining a new displacement target position for displacement to the predetermined position in subsequent observation while taking into account the positional difference stored previously and the displacement target position used at the time of storage.

In another aspect of the present invention, through provision of means for detecting positional difference between a target position on a chip pattern within an observation visual field of a microscope after displacing a sample stage thereof and a predetermined position within the visual field, means for determining a new displacement target position while correcting a displacement target position used at the moment by making use of the detection result, means for storing the new displacement target position at every determination and means for determining a new displacement target position for displacement to the predetermined position in subsequent observation while taking into account the after correction displacement target position stored previously.

When observing another wafer on which the same patterns with the same alignment as the previous one are printed or another pattern on the same wafer, the previous sample stage displacement target designation position is also modified while taking into account of the previous observation visual field position deviation which is registered to the corresponding observation position, and the stage is displaced according to the designation position.

A coordinate on a coordinate designation means for designating a position within a sample, in that a chip (which is hereinafter called as in-sample position designating coordinate) and a coordinate on the coordinate designation means for designating a chip alignment are separately provided (which is hereinafter called as alignment position designating coordinate). These sample stage coordinates give ones with reference to a fixed position with respect to the sample stage of the samples, in that chips and a supporting body, in that a wafer, mounting a plurality of the samples at the moment of registering two characteristic structures which are used for coordinate calibration performed prior to the observation and using the characteristic structures, and the ones using an arbitrary position on the wafer as an origin. However, when a wafer is again remounted on the sample stage for observation after the two portions have been registered, a deviation from the original position is caused because of limitation in mechanical origin matching accuracy between the wafer and the sample stage. In such instance, a deviation amount of a desired position for observation portion from the concerned portion after completing sample stage displacement is detected, the deviation detection result or corrected displacement target position using the result is successively stored, then, statistical processing result of these past deviation amount or the after correction displacement target positions are reflected on a newly determined displacement designation position, or re-determination of displacement designation position is performed based on these results.

On one hand, when performing an automatic observation, these positional deviation amounts are recorded in advance in the sequence file recording observation sequence including observation position while relating to the observation position. When performing an observation according to the sequence file, the positional deviation amount is reflected to the displacement designation position. The method of the reflection is as same as the one explained above. On the other hand, the microscope device, in which the positional deviation recorded in the sequence file is caused, is separated from other microscope devices. For the separation, for example, the manufacturer's serial number of the device is recorded together with the detected positional deviation amount.

After having prepared the sequence file and when the sequence file is used for another device, the device automatically reads the manufacturer's serial number and also automatically identifies the device in which the detected positional deviation is resulted. The displacement designation position is determined while only taking into account of the records of the positional deviation amounts or of the displacement target positions which are corrected every time by making use of the result of these positional deviation amounts which are confirmed as those of the concerned device. Thereby, a possible correction by making use of positional deviation detected in other device can be prevented. With the above measure, even under a circumstance where the observation sequence file is exchangeably used between different devices, a sample stage with a high positional designation accuracy can be provided.

Namely, the apparatus using charged particle beam according to the present invention, which comprises a charged particle beam source for generating charged particle beams; a sample stage which holds a sample and displaces the same; a lens which converges charged particle beams emitted from the charged particle beam source onto the sample; a deflector which deflects the charged particle beams; a picture image detection means which detects a picture image of the sample; a picture image display means which displays the picture image detected; a coordinate designation means which designates a position on the sample; means for relating a coordinate value on the coordinate designation means to a coordinate value on the sample stage while permitting calibration thereof and for displacing the sample stage to a position of the sample stage corresponding to the coordinate value designated on the coordinate designation means, is characterized in that the apparatus further comprises, a positional deviation amount calculation means which, when observing any observation position on the sample, displaces the sample stage so that a displacement target position designated by the coordinate designation means coincides with the observation position and calculates a positional deviation amount between a predetermined position on a sample which is detected by the picture image detection means after completing the displacement and a predetermined position of the picture image detection means; a memory means which stores the calculated positional deviation amount; and a positional deviation correction means which controls a displacement target position coordinate value used when displacing subsequently to an observation position corresponding to the previous observation position or the same observation position based on the positional deviation amount determined by the positional deviation amount calculation means and operates so that the predetermined position of the sample at the time when the sample stage stops and the predetermined position on the picture image display means coincide each other.

With the apparatus using charged particle beam according to the present invention, since the sample stage displacement target position is determined while taking into account in advance of the visual field deviation amount caused in the course of displacement to the position prior to the concerned observation, the stop position accuracy of the sample stage can be enhanced.

Further, the apparatus using charged particle beam according to the present invention, which comprises a charged particle beam source for generating charged particle beams; a sample stage which holds a sample and displaces the same; a lens which converges charged particle beams emitted from the charged particle beam source onto the sample; a deflector which deflects the charged particle beams; a picture image detection means which detects a picture image of the sample; a picture image display means which displays the picture image detected; a coordinate designation means which designates a position on the sample; means for relating a coordinate value on the coordinate designation means to a coordinate value on the sample stage while permitting calibration thereof and for displacing the sample stage to a position of the sample stage corresponding to the coordinate value designated on the coordinate designation means, is characterized in that the apparatus further comprises, a positional deviation amount calculation means which, when observing any observation position on the sample, displaces the sample stage so that a displacement target position designated by the coordinate designation means coincides with the observation position and calculates a positional deviation amount between a predetermined position on a sample which is detected by the picture image detection means after completing the displacement and a predetermined position of the picture image display means; means for determining after-correction displacement target position coordinate value after correcting the displacement target position coordinate value used at the moment by making use of the calculated positional deviation; a memory means which stores the determined after-correction target position; and a positional deviation correction means which controls a displacement target position coordinate value used when displacing subsequently to an observation position corresponding to the previous observation position or the same observation position based on the after-correction displacement target position coordinate value stored in the memory means and operates so that the predetermined position of the sample at the time when the sample stage stops and the predetermined position on the picture image display means coincide each other.

The apparatus using charged particle beam according to the present invention can further be provided with an observation sequence memory unit which stores such as a planed observation position, an observation portion picture image and an observation sequence and further stores the positional deviation amount or the after-correction displacement target position coordinate value while relating to the planed observation position coordinate value in the observation sequence memory unit.

Through the registration and storage of the record of the visual field deviation amount or the displacement target position corrected by the visual field deviation amount together with the observation sequence record as has been explained above, the present invention can provide a simple and proper method when repeatedly observing patterns on a same wafer or likely when repeatedly observing patterns on the same type of wafers.

Further, in the present invention, when controlling the displacement target position coordinate at the time of displacing to an arbitrary observation position, a statistically processed result of the positional deviation amounts or the after-correction displacement target position coordinate values for a plurality of times obtained previously can be used. The statistical processing can be an averaging processing. Further, the statistical processing can be a weighted averaging processing in which the positional deviation detection result obtained lately is heavily weighted. When processing the past visual field deviation amounts through the statistical processing method including the averaging and weighted averaging in which the latest amount is heavily weighted, the stop position accuracy of the sample stage can be stabilized with a high accuracy.

Further, in the present invention, means for setting in advance an effective number of traceable past positional deviation amounts calculated by the positional amount calculation means can be provided. Further, means for storing the effective number of the traceable past positional deviation amounts calculated by the positional deviation amount calculation means while relating in advance with the observation sequence memory means can be provided and only the positional deviation amount calculation result corresponding to the calculation point number set for the automatic observation can be determined valid.

By limiting the useable number of visual field deviation amounts or of displacement target positions corrected by the visual field deviation amounts at a predetermined number as has been explained above, a necessary storage capacity can be properly suppressed.

Further, in the present invention, a device identification means can be provided which identifies an apparatus using charged particle beam for which the positional deviation amount or the after-correction displacement target position coordinate value has been obtained, the positional deviation amount memory means or the after-correction displacement target position coordinate value memory means stores the positional deviation amount or the after-correction displacement target position coordinate value for every apparatus using charged particle beam identified by the device identification means while relating to the planed observation position, and when determining the displacement target position of the sample stage by the positional deviation correction means, the displacement target position of the sample stage can be determined based on the statistically processed result of the detected positional deviation amount or the after-correction displacement target position coordinate value reflected by the detected positional deviation amount.

Through the provision of device identification marks for identifying scanning type electron microscopes, a common observation sequence can be used between different devices.

In the present invention, means for switching the positional deviation correction means between valid and invalid can be provided. Further, means for storing the setting between valid and invalid of the positional deviation correction means while relating in advance with the observation sequence memory means can be provided and the valid and invalid of the positional deviation correction means at the time of automatic observation can be controlled.

In the present invention, means for switching the positional deviation amount calculation means between valid and invalid can be provided. Further, means for storing the setting between valid and invalid of the positional deviation amount calculation means while relating in advance with the observation sequence memory means can be provided and the valid and invalid of the positional deviation amount calculation means at the time of automatic observation can be controlled.

Further, the apparatus using charged particle beam according to the present invention, which comprises; a sample stage which can displace in two dimensional direction; a coordinate value designation means which designates a position on a sample; means for relating a coordinate value on the coordinate value designation means to a coordinate value on the sample stage while permitting calibration thereof and for displacing the sample stage to a position of the sample stage corresponding to the coordinate value designated on the coordinate value designation means, is characterized in that the apparatus further comprises, a target position deviation detection means for detecting in a microscope visual field a positional deviation amount between a target position designated by the coordinate value designation means and a position after displacement of the sample stage; a positional deviation amount memory means for storing the positional deviation detection result by the position deviation detection means while relating to the target position; and a position deviation correction means which determines a displacement target position of the sample stage based on a statistical processing result of the positional deviation detection result relating to the concerned target position stored previously in the positional deviation amount memory means when designating the target position by the coordinate value designation means and displacing the sample stage to the target position.

The above apparatus using charged particle beam determines the sample stage displacement target position while taking into account in advance of the visual field deviation amount caused when displacing to the concerned position prior to the observation, therefore, the stop position accuracy of the sample stage can be enhanced. The target position deviation detection means can be realized by a length measurement function which measures distance between two points on an image of the apparatus using charged particle beam obtained at the time of observation. The apparatus using charged particle beam according to the present invention shows a characteristic that the positional deviation designated by the coordinate value designation means and the position after displacement of the sample stage is gradually reduced, as the displacement of the sample stage is repeated.

DETAILED DESCRIPTION OF PREFERRED EMBODIMENTS

Hereinbelow, an embodiment of the present invention will be explained with reference to the drawings. Herein, the present invention will be explained using a scanning type electron microscope as an example of the apparatus using charged particle beam.

Figure 1:
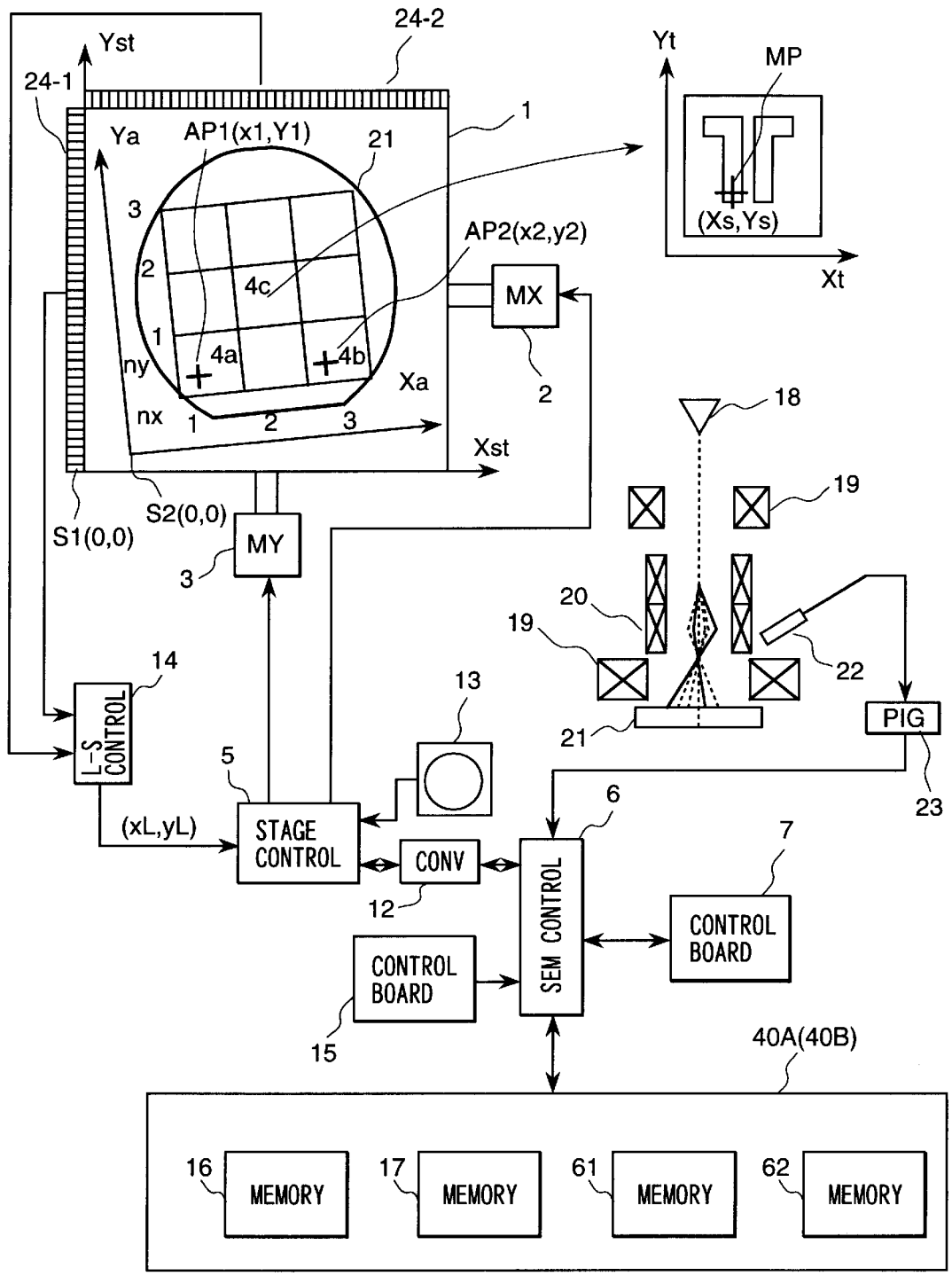
FIG. 1 is a schematic diagram of a scanning type electron microscope representing an example of apparatus using charged particle beam according to the present invention.

FIG. 1 shows a schematic diagram of a scanning type electron microscope representing an example of apparatus using charged particle beam according to the present invention. Primary electron beams are generated from an electron beam source 18, are converged by an electron lens 19 and are caused to scan over the surface of a sample 21 by a deflector 20. Secondary electrons generated at this moment are detected by a detector 22. The detection signals reflecting, in particular, such as configuration and components of the sample surface are inputted into a picture image generator 23. In that, the signals from the detector 22 are observed as an image of a scanning type electron microscope (hereinbelow will be called as SEM) at the picture image generator 23 which produces a two dimensional image in synchronism with the operation of a deflection amplifier (not shown). These arrangement is the same as those of other scanning type electron microscopes.

A sample stage 1 is driven by motors 2 and 3 in orthogonal X and Y directions. On the sample stage 1, in particular, on its movable range a plurality of samples (chips) 4a, 4b, ... of nx×ny pieces (in FIG. 1, 3×3=9) which are formed by printing on a common supporting body (wafer) are mounted. A sample stage control unit 5 can displace the sample stage 1 to any position by driving the motors 2 and 3 by a predetermined distance with reference to a mechanical origin S1 (0, 0) of the sample stage 1. In the present embodiment, chip patterns (samples) 4 of only 3×3 printed on a wafer (supporting body) 21 during a semiconductor manufacturing process are arranged.

Figure 2:
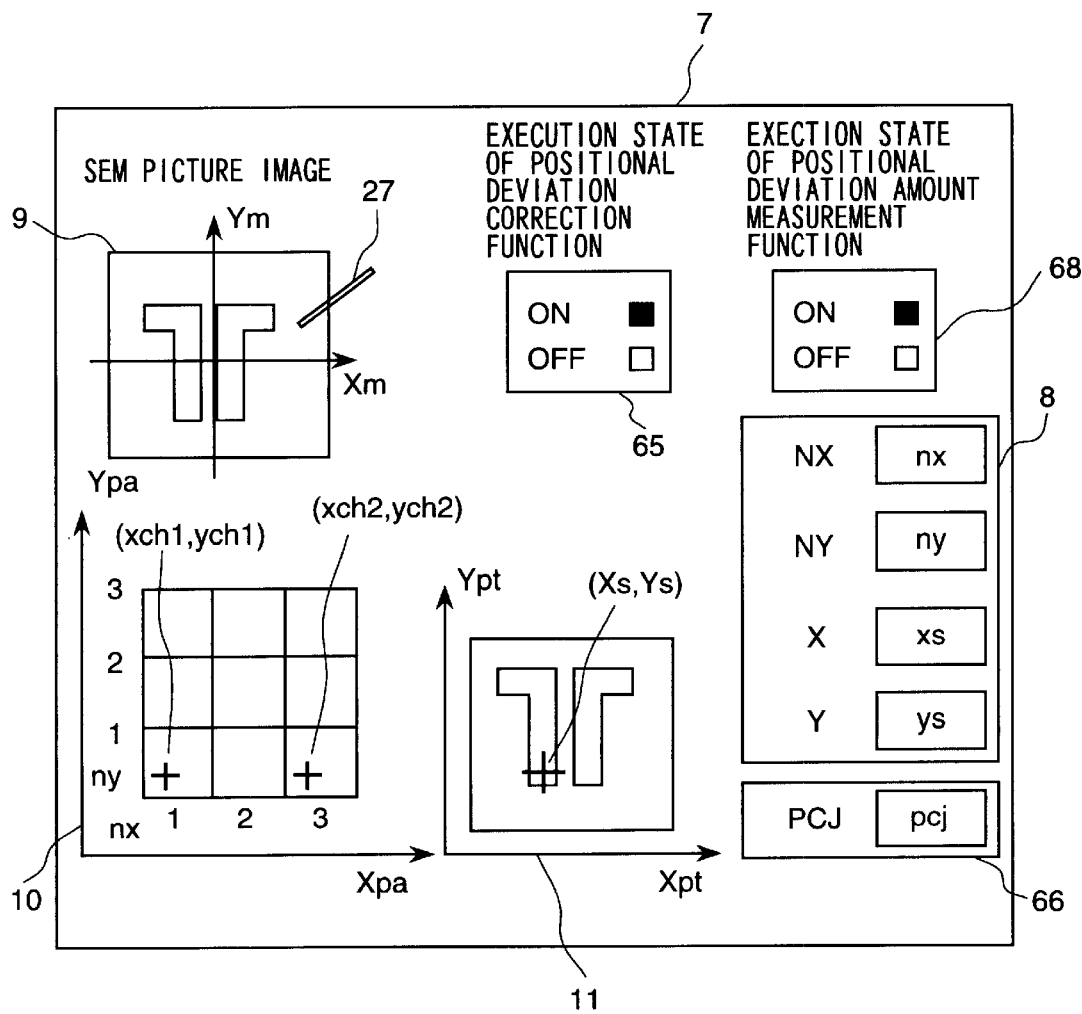
FIG. 2 is a diagram for explaining a control board (A) in FIG. 1.

As shown in FIG. 2, a control board A 7 is designed so as to permit a coordinate designation through designation of chip alignment and in-chip coordinate. When an observation position is already known by a coordinate value, the coordinate value is inputted into a coordinate value input window 8. When the coordinate value is unknown or a position on a pattern to be observed and measured is not correctly determined, the position is designated on an SEM picture image by a pointing pen 27. At such instance the chip on the current sample stage position automatically assumes the designated chip location. Accordingly, it is necessary before designating a position to displace the sample stage to a desired chip position by designating the same on a chip location coordinate 10. On the chip location designation coordinate 10 a chip location layout diagram based on a design data is drawn. Further, in an in-chip position designation coordinate 11 a chip layout based on the design data is likely drawn. Still further, the in-chip position designation can be performed on the chip location designation coordinate 10 with regard to display thereof only, and the actual designation thereof can be performed within a visual field seen in the SEM picture image 9.

The positional deviation correction function which is one of characteristics of the present invention is, in particular, effective for an observation sample in which chips of totally identical type are printed on many number of wafer pieces such as DRAMs having many manufacturing number of pieces. Namely, when performing a sampling inspection of a predetermined amount among many number of wafer pieces, the inspection is required for many number of pieces. Chips manufactured under a same semiconductor manufacturing process are considered to be printed under substantially the same condition including the chip position accuracy on the respective wafers. When it is required to observe many pieces of wafers among the wafers onto which the chip patterns are printed under the same process, corresponding same portions of chips on the respective different wafers are repeatedly observed, it is sufficient if a positional deviation caused with respect to the sample stage at the time of first observation is corrected for the subsequent observation. As a result, the generation of positional deviation at the first time, or in particular, at initial testing is corrected in the subsequent time by the above function of the present invention, the sample stage transference can be performed in a high accuracy in the subsequent observation.

However, other than the above, when number of manufacturing wafer pieces is small such as ASIC, number of inspection pieces is small, and in some cases a printing condition may be determined through one time inspection. In such instance, the function of the present invention which can not necessary increase a positional accuracy through one time inspection can not be so effective. Therefore, it is sometimes necessary to turn OFF the present function.

When there occurs high and low positional accuracies of the sample stage through ON/OFF switching of the function according to the present invention, there arises differences in area of the region on the wafer surface in which an automatic search of observation pattern performed after completing displacement of the sample stage through picture image processing is required. Namely, after the sample stage is stopped with a high positional accuracy, since the stop position already comes close to the observation pattern, the region which requires the searching is inherently narrowed. On the other hand, after the sample stage is stopped with a low positional accuracy, a large distance between the stop position and the observation pattern is still remained. A region which requires a search is inherently broadened.

Figure 6:
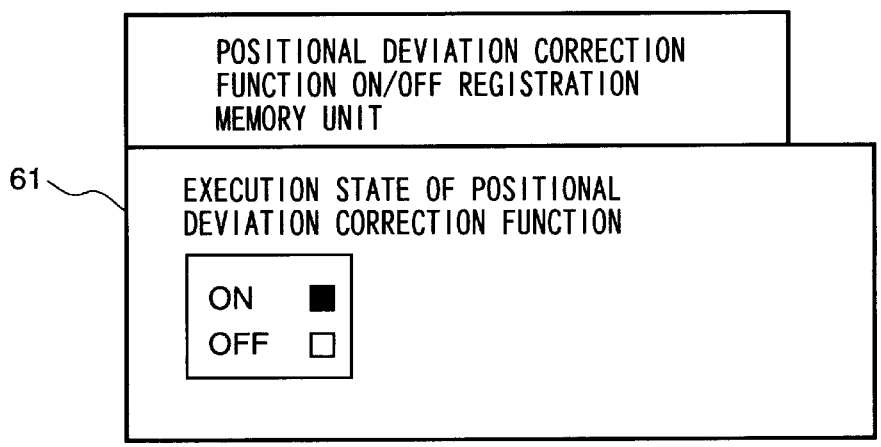
FIG. 6 is a diagram for explaining a positional deviation amount correction function ON/OFF registration and memory unit in FIG. 1.

In order to countermeasure the above problem, the present invention is further provided with a function of ON/OFF switching of a positional deviation correction function. As show in FIG. 3, a control board B 15 is added of a switch which turns ON or OFF the positional deviation correction function. Through an operation of the switch by an operator, the scanning type electron microscope of the present invention can be operated while either validating or invalidating the positional deviation correction function. Further, as shown in FIG. 2, the control board A 7 is provided with a positional deviation correction function executing state indicator 65 which tells to the operator the current executing state of the positional deviation correction function. Therefore, the operator can perform the operation while recognizing whether there is an error with respect to function selection which varies depending on kinds of samples to be observed. On the other hand, in the present invention, other than the manual operation, an automatic observation can be performed through a control unit such as a computer according to a sequence (a recipe) recorded in an observation sequence memory unit 40A (40B). In the present invention, the observation sequence memory unit 40A (40B) is provided with a positional deviation correction function ON/OFF registration and memory unit 61. As shown in FIG. 6 in the positional deviation correction function ON/OFF registration and memory unit 61 the ON/OFF state thereof is registered which permits ON/OFF switching of the positional deviation correction function execution state at the time of automatic observation by making use of the observation sequence memory unit 40A (40B).

Further, when executing the positional deviation correction function, the effect of correction, in that the observation result can be varied how far the past positional deviation amount measurement result to be used for the correction is to be traced back depending on the kinds of samples to be observed. Namely, when, for example, an observation surface is likely to be charged up by an electron beam irradiation, a phenomenon is caused in which due to a potential distribution distortion caused by residual charges and due to momentarily varying condition the sample surface in the visual field now being observed through the scanning type electron microscope varies moment by moment which is called as a drift. For example, when observing samples which show frequent and large drift phenomenon, an indefinite variation with regard to positional relationship between the sample stage and the visual field of the scanning type electron microscope is always caused, and for example such variation tends to shift every moment to a certain direction. When an influence of such drift phenomenon affecting on positional deviation is large, and if the function of the present invention traces back long to the past positional deviation amount measurement result, the deviation contained in the deviation amount becomes large, and the sample stage transference to a correct position which is the primary object of the present invention can not be effected. Accordingly, in the present invention a function is added which adjusts number of positional deviation amount measurement points according to judgement of an operator and depending on the samples to be observed by limiting the number of positional deviation amount measurement result to be traced back to the past, in other works by limiting the time interval corresponding to the measurement point number because the sampling is performed for a predetermined interval. In the present invention, an effective data point number pcj of positional deviation correction is displayed on the control board A 7 as shown in FIG. 2 and further an effective correction data point number input window is provided which serves as an input window for inputting pcj by the operator at the same time.

Like the ON/OFF switching of the positional deviation correction function, an automatic observation may be performed by means of the control unit such as a computer according to the sequence (recipe) recorded in the observation sequence memory unit 40A (40B). In the present invention, the observation sequence memory unit 40A (40B) is provided with a used positional deviation amount correction point number registration and memory unit 62 as shown in FIG. 1. In the used positional deviation amount correction point number registration and memory unit 62 an effective or valid data point number pcj for positional deviation correction is recorded under a condition that the data point number can be read out depending on necessity while permitting writing when storage thereof is required.

As one of modifications of the present invention, after successively performing measurement of positional deviation amount for a predetermined period in the past, a displacement target position is corrected at a certain time point by making use of the measurement result to determine a new displacement target position, thereby, the positional accuracy of the sample stage at the time of displacement is enhanced thereafter.

Figure 3:
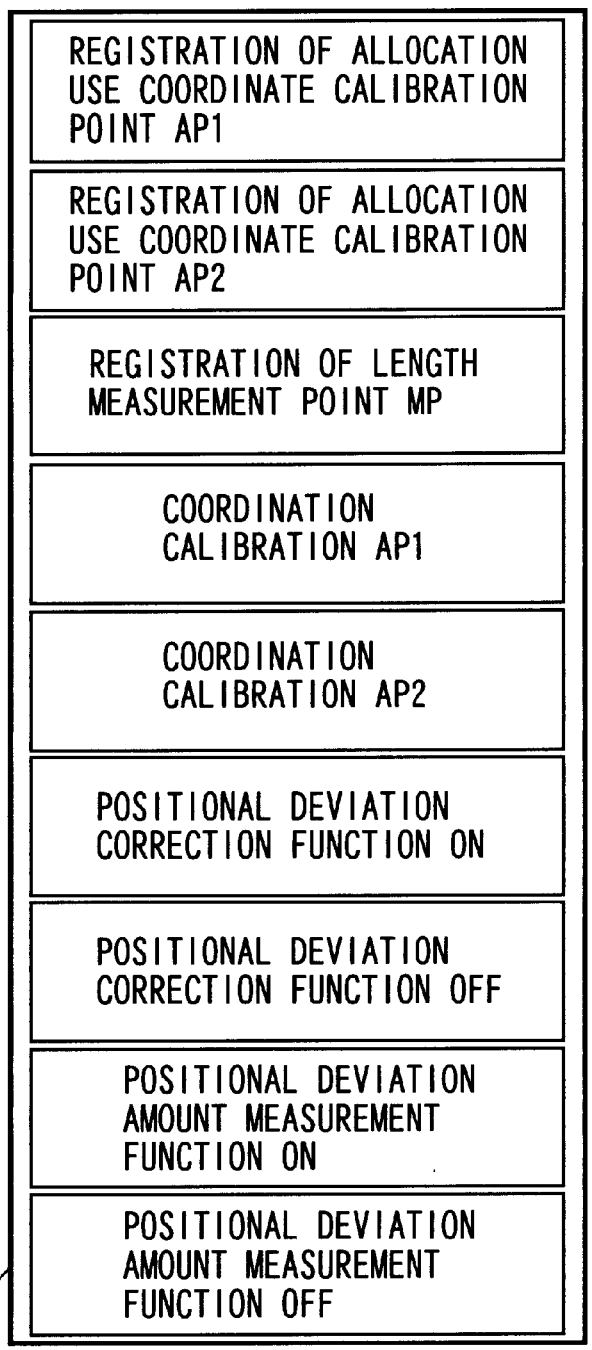
FIG. 3 is a diagram for explaining another control board (B) in FIG. 1.

In the present invention, the above is achieved by a function which turns ON or OFF the positional deviation amount measurement function. As shown in FIG. 3, a switch which turns ON or OFF the positional deviation measurement function is added to the control board B 15. The scanning type electron microscope of the present invention can be operated while validating or invalidating the positional deviation amount measurement function through manipulation of the switch by an operator.

Further, as shown in FIG. 2, the control board A 7 is provided with a positional deviation amount measurement function execution state indicator 68 so as to tell the operator the execution state at the moment of the positional deviation amount measurement function. Thus, the operator can operate the scanning type electron microscope along with the purpose of observation at every moment while confirming whether no function selection errors are made.

Figure 12:
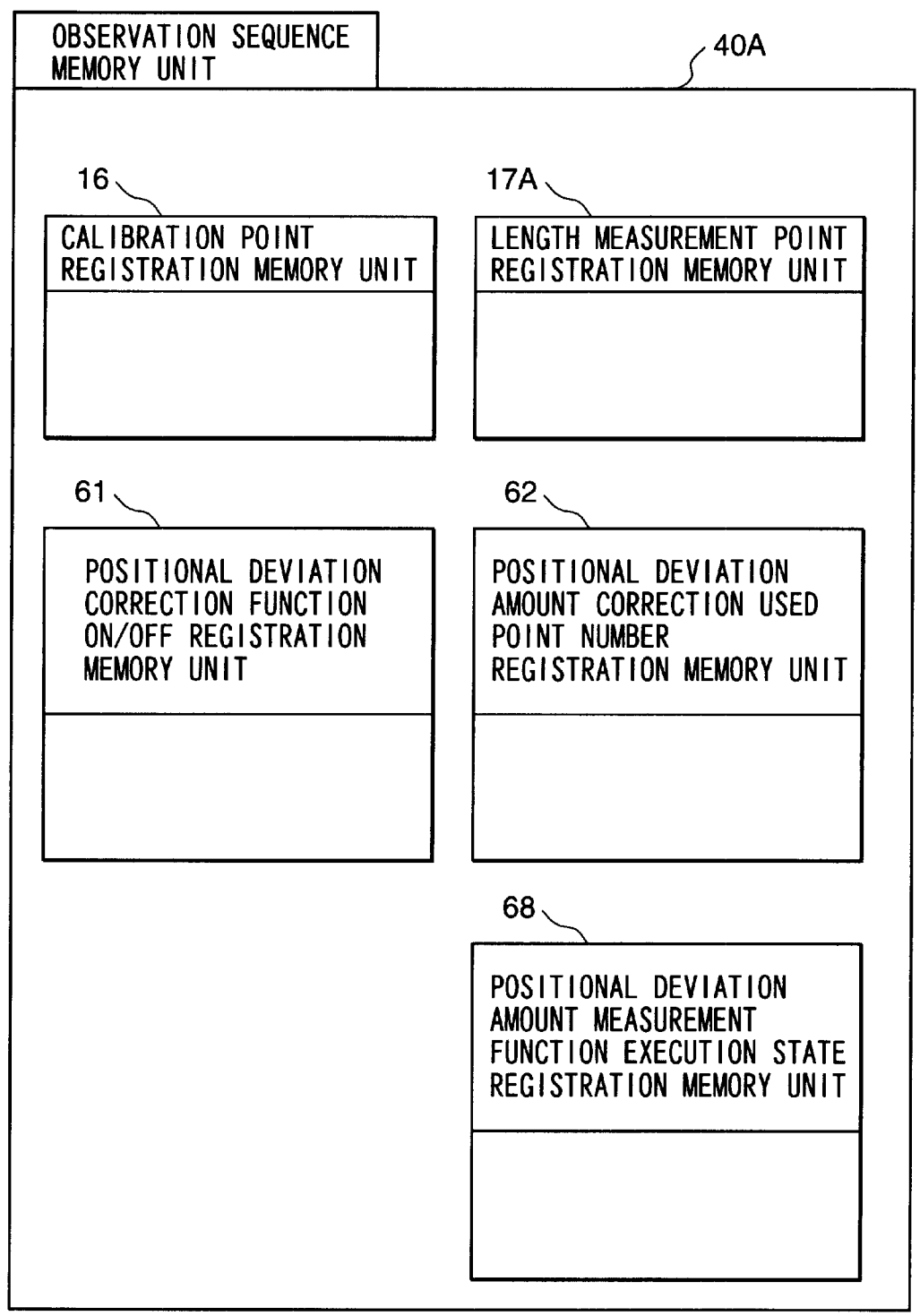
FIG. 12 is a diagram for explaining an observation sequence memory unit in FIG. 1.
Figure 21:
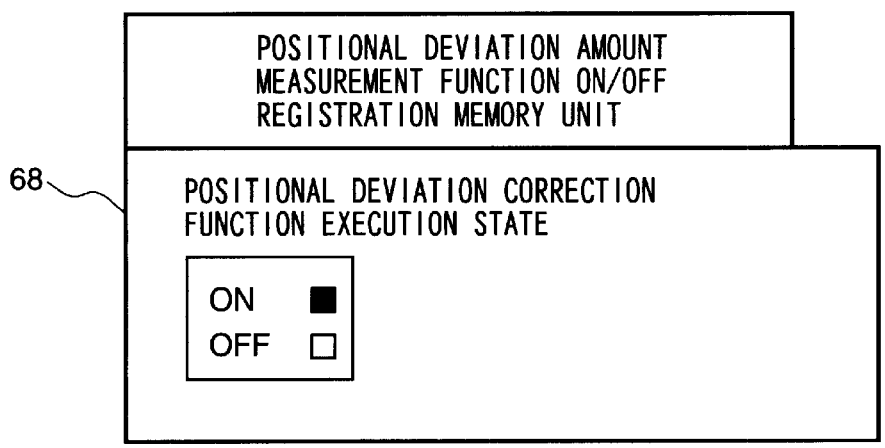
FIG. 21 is a diagram for explaining a positional deviation amount measurement function ON/OFF registration and memory unit in FIG. 2.

Other than the manual operation of the scanning type electron microscope of the present invention, with the scanning type electron microscope of the present invention, an automatic observation can be performed through a control unit such as a computer according to a sequence (recipe) recorded in the observation sequence memory unit 40A (40B) as shown in FIG. 12. In the present invention, the observation sequence memory unit 40A (40B) is provided with a positional deviation amount measurement function ON/OFF registration and memory unit 68. In the positional deviation amount measurement function ON/OFF registration and memory unit 68 an ON/OFF state is registered as shown in FIG. 21 and switching of the ON/OFF execution state of the positional deviation amount measurement function is permitted when an automatic observation is performed by making use of the observation sequence memory unit 40A (40B).

The above functions can be realized in softwares which drive the SEM control unit 6 for the main body of scanning type electron microscope. Accordingly, the present invention includes a variety of control boards other than the physical control board as shown in FIG. 1. An operator can view a concerned display on the screens of the control boards A and B 7 and 15 as well as can provide a necessary command thereon. On the control board 7 an in-chip coordinate value (xs, yx) of an observation portion and an location position (nx, ny) of the sample to be observed which are in advance registered are outputted. Then, a distance of the concerned position from the origin position S2 (0, 0) of a designation coordination Xa-Ya is outputted from a coordinate value converter 12.

In order to move the sample stage through manual operation, such as a track ball 13 serving as switches and the like is further connected to the stage control unit 5. When the track ball 13 is manipulated, the motor 2 or 3 is driven so as to displace the sample stage 1 according to the rotation thereof.

When a displacement command is executed in response to a designation by the operation with the track ball 13 or the control board A 7, the stage control unit 5 receives a read coordinate value on a linear scale 24 from a linear scale controller 14, and drives the motors 2 and 3 until the read coordinate value coincides to a value corresponding to a displacement designation value (xst, yst).

Depending on necessity the operator presses a variety of switches on the control board B 15 to cause to execute a necessary function at every moment. FIG. 3 shows a layout of the variety of switches. When the operator presses a registration switch of allocation use coordinate calibration point AP1 the SEM control unit 6 reads the position at the moment on the liner scale 24 of the sample stage, and registers and stores the read value in the calibration point registration unit 16. Further, when a registration switch of the allocation use coordinate calibration point AP2 is pressed, a registration and storage are effected in the same manner as with AP1. On one hand, when a registration switch of length measurement point MP is pressed, the position at the moment on the linear scale 24 of the sample stage is read in the same manner as in the calibration point registration and the read value is registered and stored in the length measurement point registration and memory unit 17. In connection with the above referred to switches, when the operator presses a switch, the position at the moment for respective purpose of the sample stage is registered and stored.

When a wafer is again mounted for observation on the sample stage after the above referred to registration operation and the operator presses the registration switch of coordinate calibration AP1, the position registered and stored through the above operation is related with the position at the moment of the sample stage. Further, with regard to the coordinate calibration AP2 the position registered and stored is likely related with the position at the moment of the sample stage. After completing the relating with regard to AP1 and AP2, the coordinate calibration between designation coordinate Xa-Ya and stage coordinate Xst-Yst is performed so as to automatically designate the observation position.

When the operator presses an ON/OFF switch of positional deviation correction function, the positional deviation correction function is turned ON or OFF. Further, when the operator presses an ON/OFF switch of positional deviation amount measurement function, the function of executing measurement of positional deviation amount with regard to visual field position is turned ON or OFF for every displacement completion of the sample stage.

On one hand, in the observation sequence memory unit 40A as shown in FIG. 12 a variety of data for executing automatic length measurement sequence are stored. In the calibration point registration and memory unit 16 and the length measurement point registration and storage unit 17 which are included in the observation sequence memory unit 40A, for example, in-chip position coordinate value (xa, ya), (xm, ym) and chip allocation position (nxa, nya), (nxm, nym) with regard to calibration point AP and length measurement point MP used when performing the automatic length measurement sequence and SEM picture image record used when performing position identification through picture image collation are registered according to intention of the operator.

Figure 4:
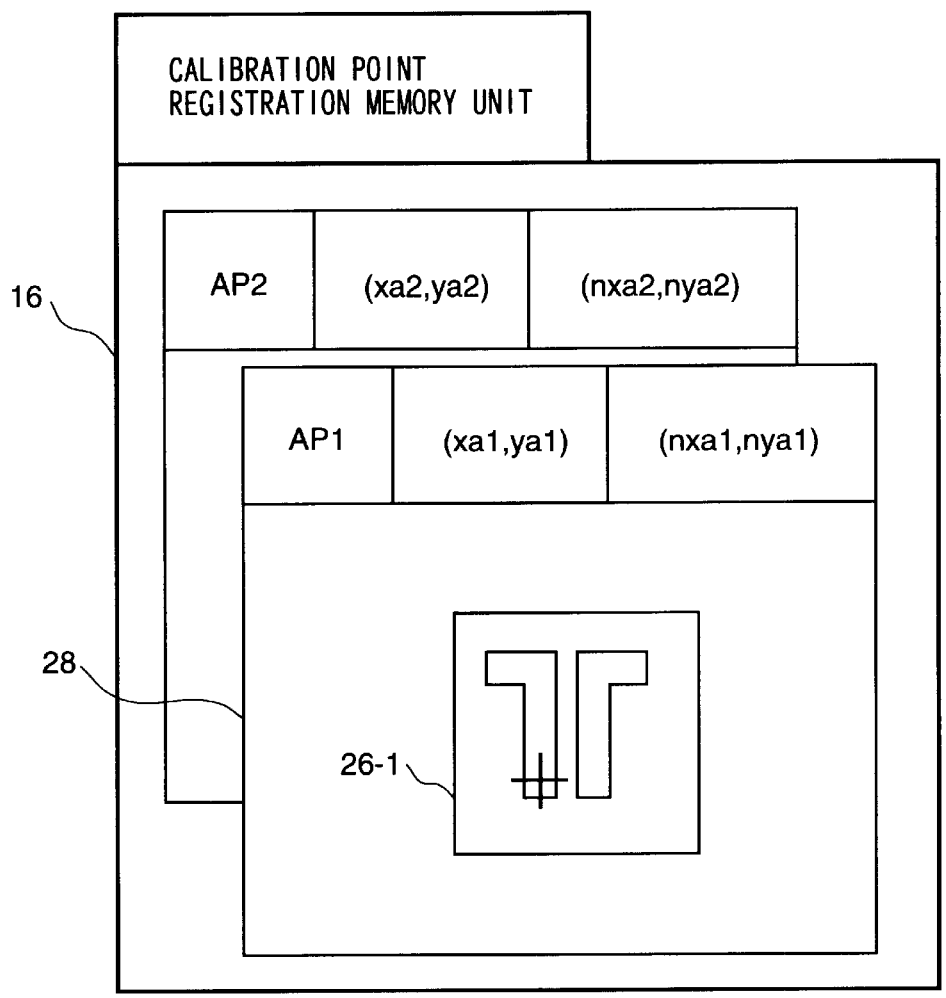
FIG. 4 is a diagram showing an example of calibration point registration and memory unit in FIG. 1.
Figure 5:
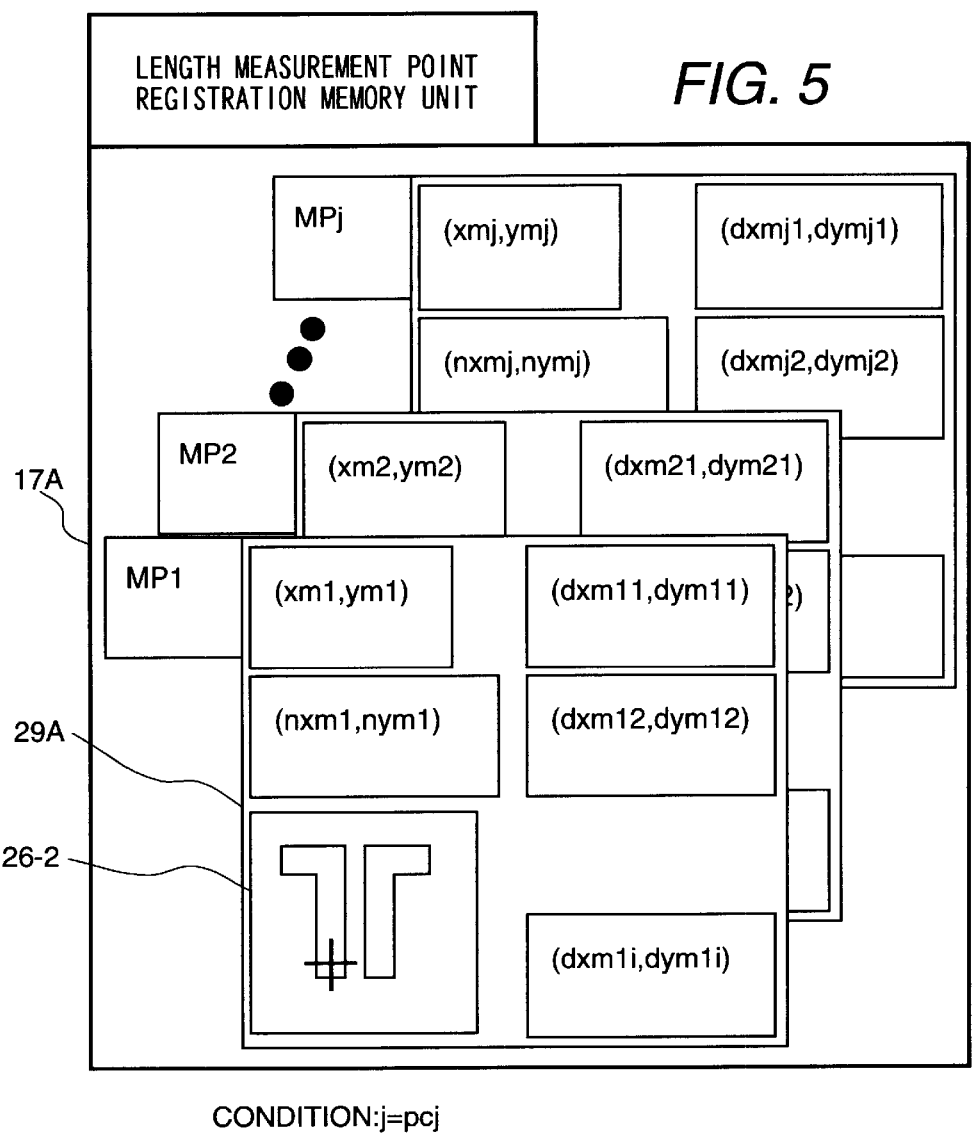
FIG. 5 is a diagram showing an example of length measurement point registration and memory unit in FIG. 1.

FIG. 4 shows an example of calibration point registration and storage units. In the calibration point registration and storage unit 16, AP1, AP2, . . . of which number corresponds to that of the calibration points and information for respective calibration points which is necessary for performing an automatic observation are registered. For example, with regard to AP1 an observation point on the wafer 21 is displaced to a certain chip including AP1, the observation position is specifically designated on the SEM image by the pointing pen 27 and the determined observation position is converted into an in-chip coordinate value and is registered. Namely, the SEM control unit 6 determines the position of a portion desired to be observed after converting the position into in-chip coordinate value (xa, ya) of the position designated by the pointing pen 27 from sample stage coordinate value (xst, yst) and chip allocation (nx, ny) at the moment. The thus determined in-chip coordinate value (xa, ya) and chip allocation (nx, ny) are registered and stored together with the image of the observation portion used for picture image collation as shown in FIG. 5. The same is true with regard to AP2.

FIG. 5 shows an example of length measurement point registration and memory unit. In the length measurement point registration and storage unit 17A, MP1, MP2 . . . , MPj of which number corresponds to that of the length measurement points and information for respective length measurement points which is necessary for performing an automatic observation are registered. For example, with regard to MP1 an observation position on the wafer 21 is displaced to a certain chip including MP1, the observation position is specifically designated on the SEM image by the pointing pen 27 and the determined observation position is converted into an in-chip coordinate value and is registered. Namely, the SEM control unit 6 determines the position of a portion desired to be observed after converting the position into in-chip coordinate value (xm, ym) of the position designated by the pointing pen 27 from sample stage coordinate value (xst, yst) and chip allocation (nx, ny) at the moment. The thus determined in-chip coordinate value (xm, ym) and chip allocation (nx, ny) are registered and stored together with the image of the observation portion used for picture image collation as shown in FIG. 5. The same is true with regard to MP2, . . . , MPj.

Now, when repeating the displacement of the sample stage by a predetermined number of times to an observation position represented by in-chip coordinate value (xm, ym) and chip allocation (nx, ny), residual visual field positional deviation amounts after completing displacement of the sample stage to respective displacement target positions are registered and stored for respective length measurement points MP1, MP2, . . . , MPj depending on the observation times. For example, with regard to MP1, the visual field positional displacement amounts (dxm11, dym11), (dxm12, dym12), . . . , (dxmli, dymli) which covers displacement of i times are registered and stored. The same is turn with regard to MP2, . . . , MPj.

Figure 7:
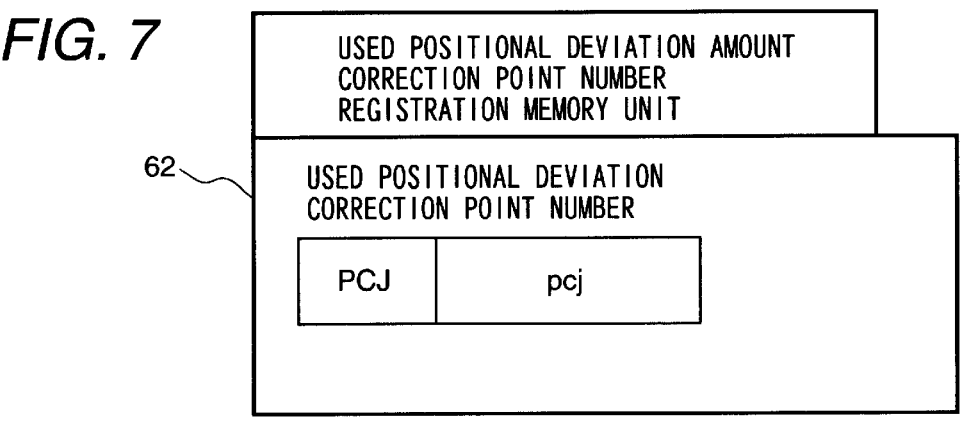
FIG. 7 is a diagram for explaining a use point number registration and memory unit for positional deviation amount correction in FIG. 1.
Figure 8:
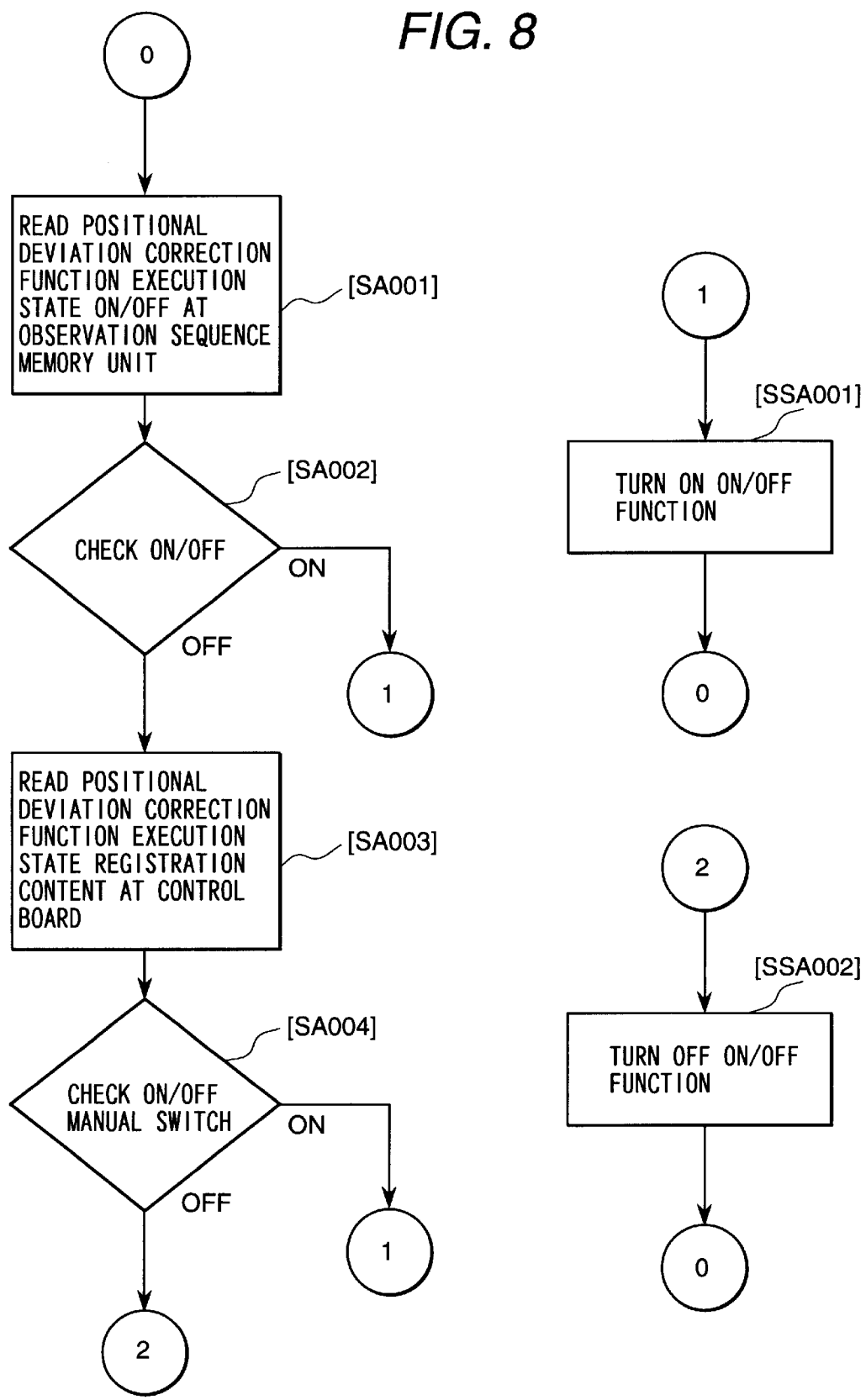
FIG. 8 is a flow chart showing an example of processing sequence performed in FIG. 1.

On the other hand, the observation sequence memory unit 40A (40B) is provided with a positional deviation correction function ON/OFF registration and memory unit 61 and a positional deviation correction use point number registration and memory unit 62 which are used so as to realize the positional deviation correction function according to the present invention at the time of executing the automatic length measurement sequence. These are shown in FIGS. 6 and 7. These functions are performed in the sequence shown in FIG. 8 in the course of performing the automatic length measurement sequence. Namely, in the following manner;

Step SA 001: Reading of ON/OFF registration content which is stored in the observation sequence memory unit Step SA 002: ON/OFF checking according to the result of step SA 001

Step SA 003: Reading of the registration content of the positional deviation correction function execution state in the control board A Step SA 004: ON/OFF checking according to the result of step SA 003

Step SSA 001: Turn ON the positional deviation correction ON/OFF function

Step SSA 002: Turn OFF the positional deviation correction ON/OFF function.

Figure 22:
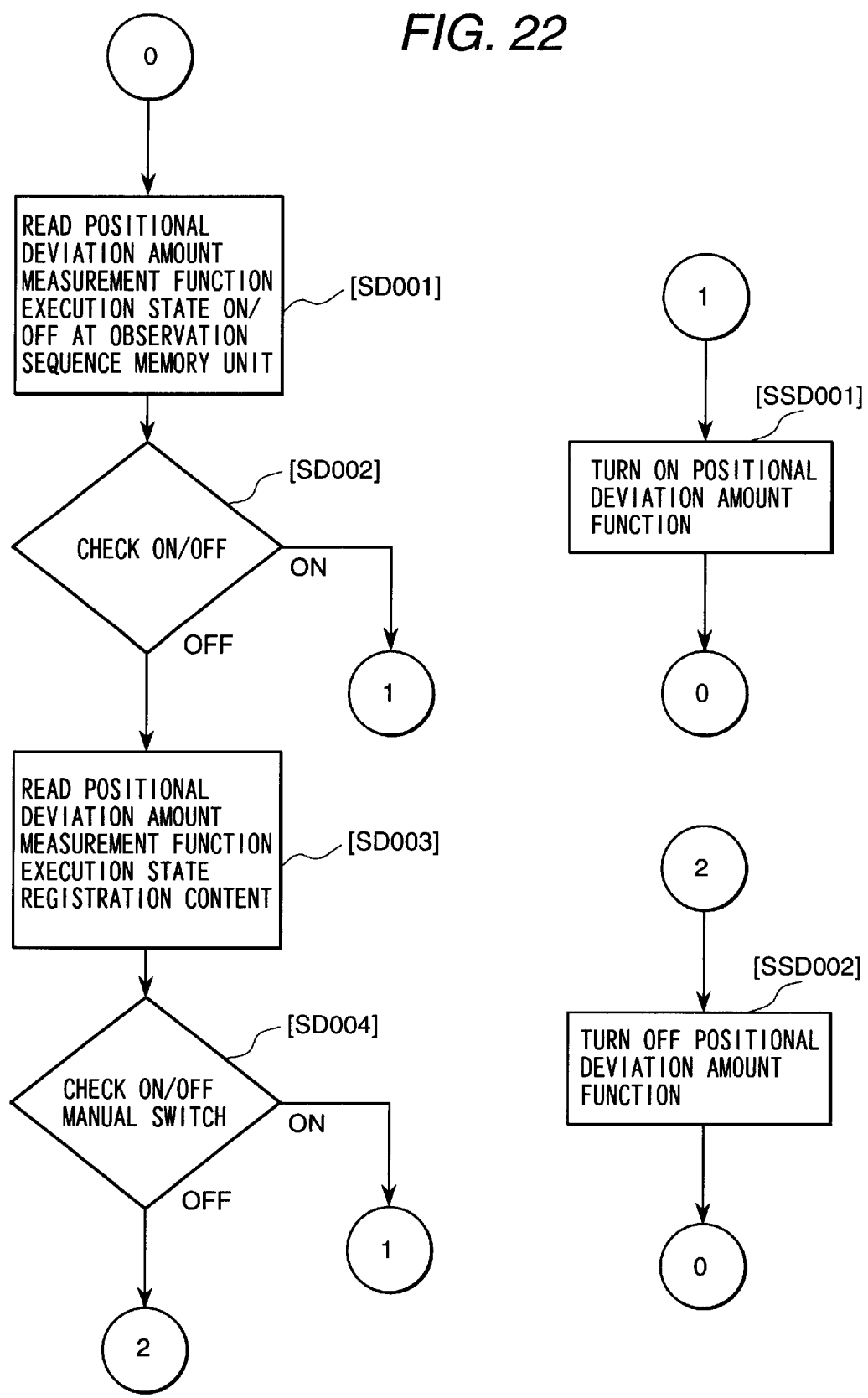
FIG. 22 is a flow chart showing an example of operation sequence performed in FIG. 1.

Further, the observation sequence memory unit 40A(40B) is provided with a positional deviation amount measurement function ON/OFF registration and memory unit 68 which is used to determine or set in advance whether the positional deviation amount measurement is to be performed in parallel with the execution of the automatic length measurement sequence. The unit is shown in FIG. 21. The function thereof is performed with the sequence shown in FIG. 22, which will be explained as follows;

Step SD 001: Reading of the execution state ON/OFF of the positional deviation amount measurement function which is stored in the observation sequence memory unit Step SD 002: Checking of ON/OFF according to the result of step SD 001

Step SD 003: Reading of execution state registration content of the positional deviation amount measurement function in the control board A Step SD 004: Checking of ON/OFF manual switch according to the result of step SD 003

Step SSD 001: Turn ON the positional deviation amount measurement function

Step SSD 002: Turn OFF the positional deviation amount measurement function.

Figure 9:
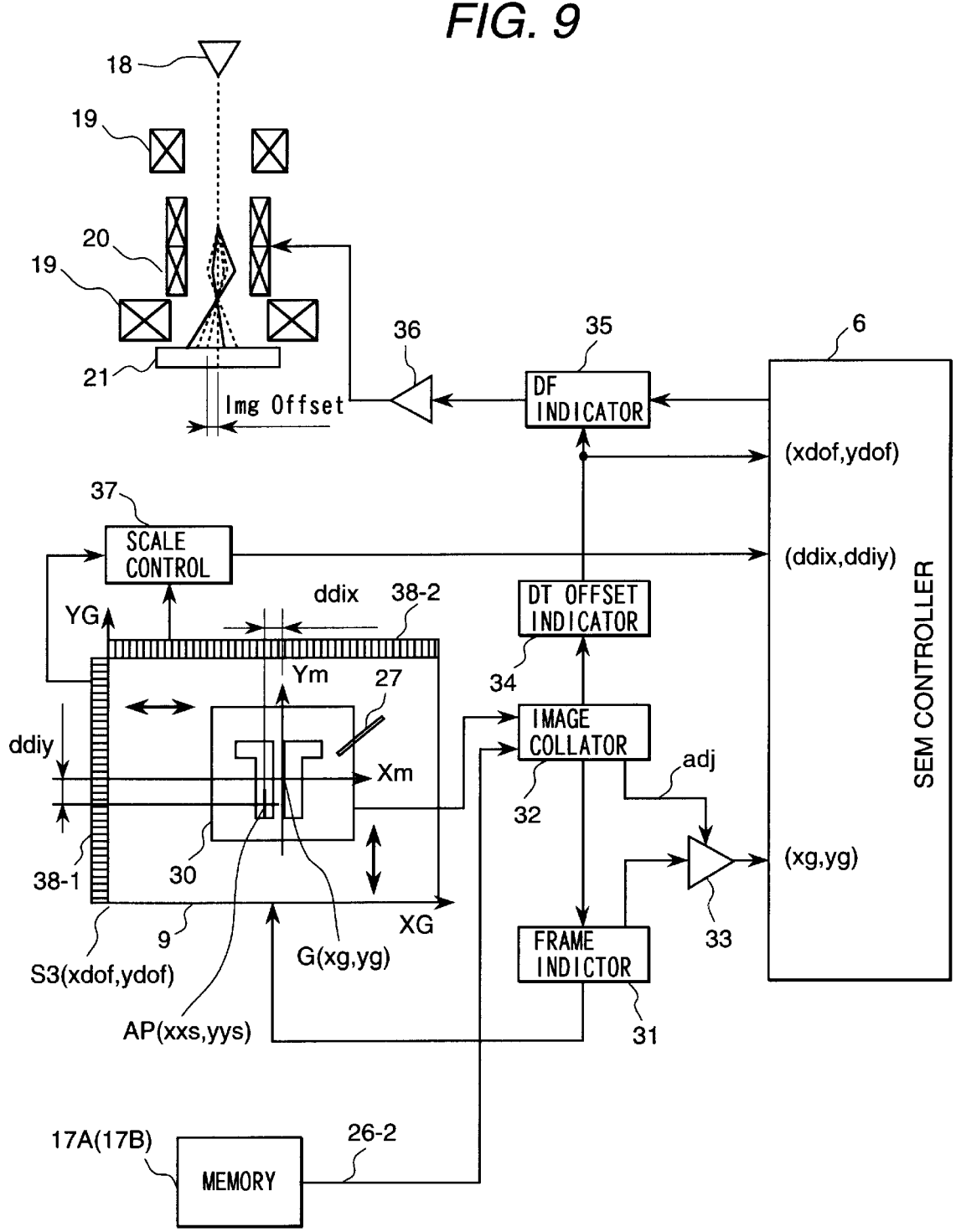
FIG. 9 is a diagram showing an arrangement for determining length measurement point position through picture image collation.

FIG. 9 shows an arrangement which determines a length measurement position through picture image collation. The picture image memory 9 which captures SEM picture images includes a variety of images other than target patterns. Any region in the picture image memory 9 having the same size as the SEM image (hereinafter will be called as a picture image frame 30) which is registered in advance in the length measurement point registration and memory unit 17, for example, at MP1 and is used for specifying the length measurement point position is allocated from the picture image memory 9 according to a command from a picture image frame position indicator 31 and sends the same to a picture image collation unit 32.

In the picture image collation unit 32, a correlation value between a picture image 26-2 registered in the length measurement point registration and memory unit 17 and the allocated image is obtained to determine a coincidence degree. If the coincidence degree exceeds a predetermined level value, "coincidence" is judged, then an ON signal adj at the time of picture image collation coincidence is turned on, and a picture image position (xg, yg) which is designated by the picture image frame position indicator 31 at this moment is outputted from the gate 31 to the SEM control unit 5. Wherein (xg, yg) is a value on a coordinate XG-YG in the picture image memory 9 including entire picture image corresponding to a primary electron beam scanning range.

On one hand, a deflection offset amount indicator 34 outputs to a deflection indicator 35 a coordinate value (xdof, ydof) representing a position on a sample of the primary electron beam scanning range at this moment. The deflection indicator 35 varies an offset amount, which is added to a "saw tooth wave" signal having an amplitude value interlocked with an SEM image magnification rate generated by the SEM control unit 6, so as to interlock with the coordinate value (xdof, ydof) and further freely varies the scanning position of the primary electron beam on the sample to be scanned by means of the deflector 20. Actually, in order to eliminate problems such as errors caused at the time of amplification by an amplifier 36, another deflector is prepared through which deflection corresponding to the offset amount for the primary electron beam is effected. To the latter deflector the "saw tooth wave" of the magnification interlocking amplitude is applied as it is.

With the above explained series of operations, if no "coincidence" of the picture image is obtained, the ON signal adj at the time of picture image collation coincidence is turned OFF to close the gate 33, and no position signal (xg, yg) is outputted. Further, at this instance the picture image frame position indicator 31 is displaced either in x direction or in y direction only by one step and the above series of picture image collation operation is again repeated. If the displacement of the picture image frame has covered all of the regions on the picture image memory and no new places for the displacement remain, the picture image collation unit 32 outputs a signal commanding to change the offset amount to the deflection offset amount indicator 34.

The deflection offset amount indicator 34 varies the offset amount of the deflection signal either in x direction or in y direction only by one step. If no "coincidence" of the SEM picture image can be obtained even after the scanning range has been displaced over the entire scannable range of the primary electron beam, the SEM control unit varies the designation position to the stage control unit 5 so as to displace the sample stage position either in x direction or in y direction only by one step. With the above series of operations an SEM image which reproduces a characteristic pattern specifying the length measurement point position is searched.

When an objective pattern on the SEM image is extracted, the calibration point position (cross mark) on the SEM image which is stored in the calibration point registration and memory unit 16 is specified, therefore, distance (ddix, ddiy) from the coordinate origin (for example, the center of gravity of the picture image frame) on the picture image frame is automatically determined with the scale 38 belonging to the picture image memory 9, and is outputted by a scale controller 37 which controls the scale 38 to the SEM control unit 6. On the other hand, the deflection offset amount indicator 34 outputs a signal (xdof, Ydof) representing an offset amount in the deflection scanning range at this moment to the SEM control unit 6.

With the series of operation until now, all of the coordinate values which are necessary to determine the position of the concerned length measurement point, in that (xg, yg), (xdof, ydof) are inputted into the SEM control unit 6. At first the position (xm, ym) of the picture image frame expressed by the designation coordinate Xa-Ya placed on the wafer is determined by making use of (xg, yg) and (xdof, ydof) according to the following equations (2), wherein f1 and f2 are functions representing a conversion from the right-hand member to the left-hand member in the equations.

$$\left. \begin{array}{l} xm = f1(xdof, xg) \\ ym = f2(ydof, yg) \end{array} \right\} \qquad (2)$$

Further, the position (xxst, yyst) of the length measurement point expressed likely by the designation coordinate Xa-Ya is determined by making use of (xm, ym) determined in the above and (ddix, ddiy) according to the following equations (3), wherein f3 and f4 are functions representing a conversion from the right-hand member to the left-hand member in the equations.

$$\left.\begin{array}{l} xxst = f3(xm,\ ddix) \\ yyst = f4(ym,\ ddiy) \end{array}\right\} \quad (3)$$

Figure 11:
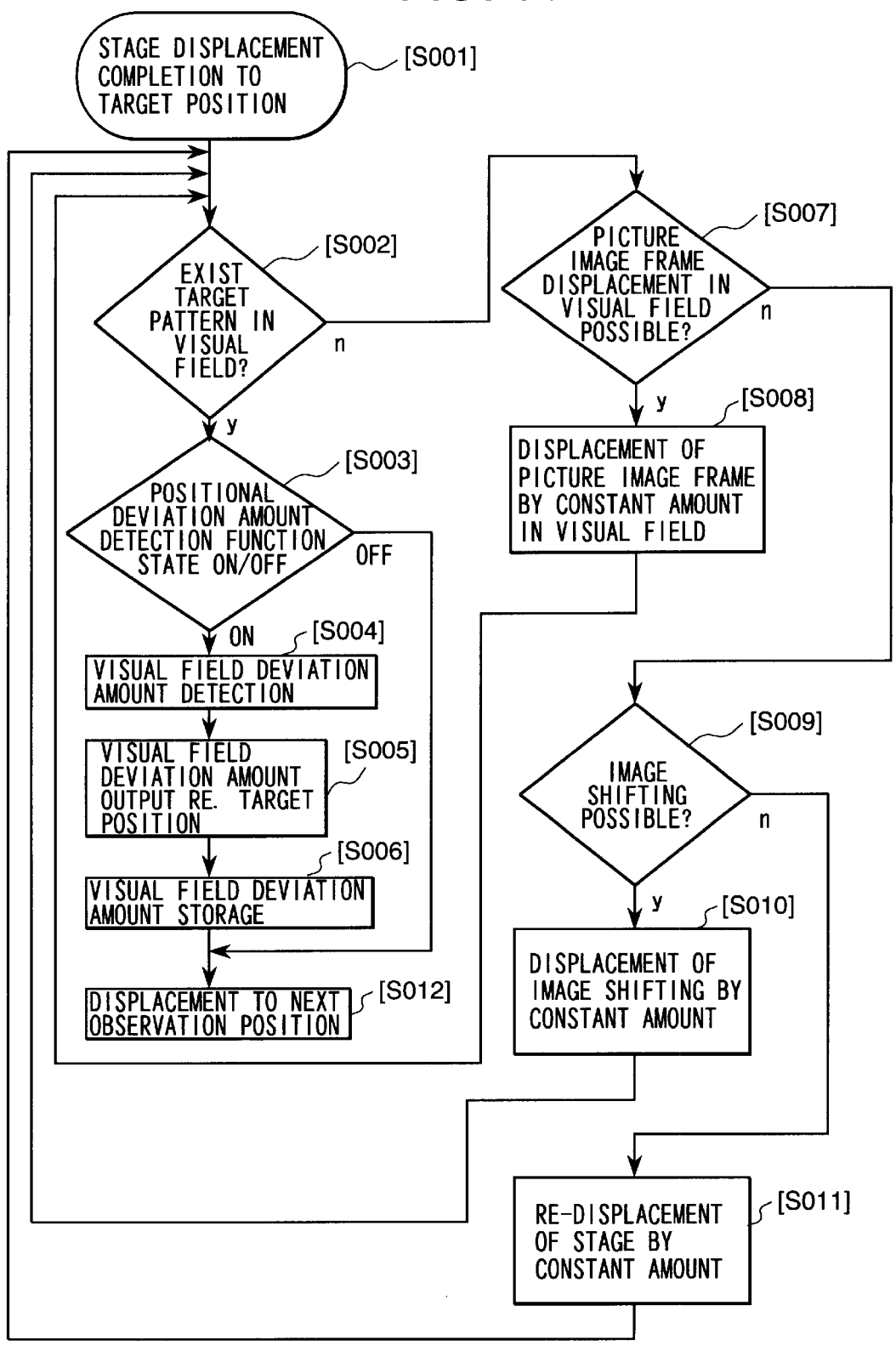
FIG. 11 is a flow chart showing an example of operation sequence performed in FIG. 1.

FIG. 11 shows a flow chart of the above operation sequence, of which flow chart shows a series of processing flow for determining a visual field deviation amount after completing the stage displacement to a target position.

Step S 001: Completion of the stage displacement to a target position

Step S 002: Is there the target pattern within visual field?

Step S 003: ON/OFF state of positional deviation amount detection function

Step S 004: Detection of visual field deviation amount

Step S 005: Outputting the visual field deviation amount with respect to a target position Step S 006: Registration and storage of the visual field deviation amount Step S 007: Is it possible to newly displace the picture image frame within the visual field?

Step S 008: Displacing the picture image frame by a constant amount within the visual field Step S 009: Is it possible to newly displace the scanning range by image shifting?

Step S 010: Displacement by the image shifting by a constant amount

Step S 011: Displacement of the stage by a constant amount

Step S 012: Displacement to subsequent observation position.

The above searching operation is basically the same for an identification of the coordinate calibration point position.

Figure 10:
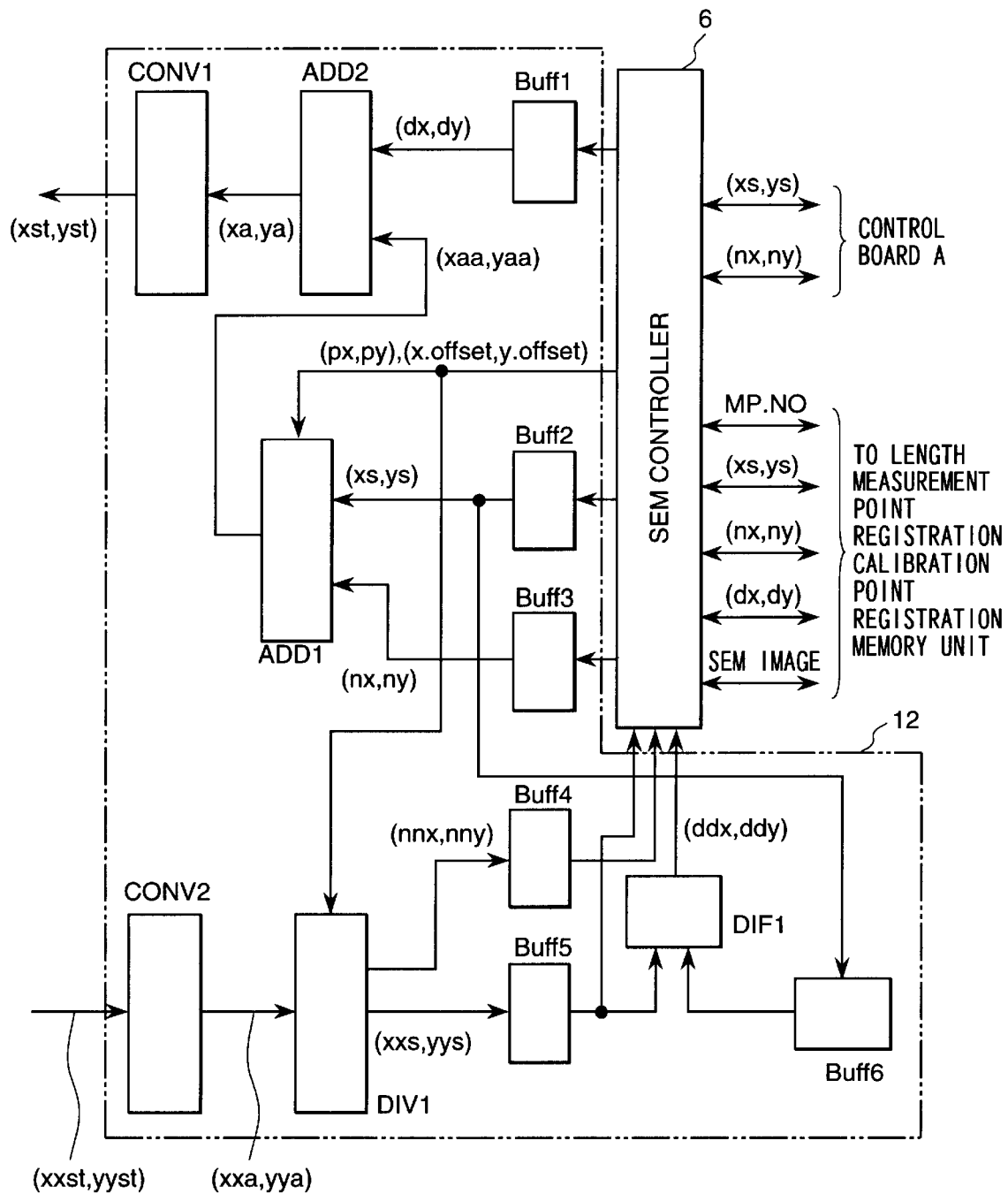
FIG. 10 is a diagram showing an arrangement of coordinate value conversion between stage coordinate and designation coordinate in FIG. 1.

FIG. 10 shows an arrangement of the coordinate value conversion between stage coordinate Xst-Yst and designation coordinate Xa-Ya.

The inside of two dotted chain line shows the structure of the coordinate value convertor 12.

The SEM control unit 6 receives signals (xs, ys), (nx, ny) designating an observation position from the control board A 7, and MP.NO representing length measurement point number NO., (xs, ys), (nx, ny) representing the observation position, (dx, dy) representing a visual field deviation until the present observation at the concerned position and SEM picture image used for identifying the length measurement point position from the length measurement point registration and memory unit 17A. These values are outputted from the SEM control unit 6, in that in the opposite direction as above, depending on necessity, for example when these values are required to be displayed on a display board and when these values are required to be registered and stored.

The SEM control unit 6 receives these data and outputs for the first time (xs, ys), (nx, ny) representing the observation position via Buff 2 and Buff 3 to ADD 1. The ADD 1 outputs a provisional designation coordinate value (xaa, yaa) based on a pitch (px, py) representing a chip design information and offset amount (xoffset, yoffset). The visual field deviation amount (dx, dy) outputted via Buff 1 is calculated by ADD 2 together with the above provisional designation coordinate value (xaa, yaa) to form a designation coordinate value (xa, ya). The designation coordinate value (xa, ya) is converted in CONV 1 into a stage coordinate value (xst, yst) and is outputted to the sample stage control unit 5.

The above series of flow shows an operation sequence when designating the coordinate value of the observation position from the SEM control unit 6 to the stage control unit 5. Herein, it is required to return in opposite direction the stage coordinate value read from the linear scale 24 to the side of the SEM control unit 6, in which stage coordinate value (xxst, yyst) representing the read coordinate value of the linear scale 24 is at first converted by CONV 2 into a designation coordinate value (xxa, yya). Like the ADD 1, DIV 1 receives the pitch (px, py) representing the chip design information and offset amount (xoffset, yoffset) from the SEM control unit 6 and converts the current sample stage position (xxa, yya) into one expressed by the chip alignment (nnx, nny) and the in-chip coordinate value (xxs, yys) based on the received values. The in-chip coordinate value (xxs, yys) is used to calculate a difference (ddx, ddy) in DIF 1 from the coordinate value (xs, ys) with regard to the observation position received at Buff 6 and being designated from the SEM control unit 6 to the stage control unit 5. The difference (ddx, ddy) represents a distance of actually caused positional deviation on the observation visual field from the designated observation position. Thus obtained (ddx, ddy), (xxs, yys) and (nnx, nny) are processed to be registered and stored such as in the length measurement point registration and memory unit 17A and the calibration point registration and memory unit 16.

In the above embodiment, the stored positional deviation amounts which were obtained in a predetermined interval in the past are used from a certain time point for correcting the sample stage displacement target position.

On the other hand, another embodiment can be used in which after every displacement completion to an observation position in the sample stage, the displacement target position used for the concerned displacement is corrected every time by making use of the measured positional deviation amount to determine a new after-correction displacement target position and to store the same successively, and in which embodiment, when displacing subsequently to the same portion or corresponding observation position, a new displacement target position is determined through a statistical processing of the past after-correction displacement target positions stored until that moment.

The present embodiment is different from the previous embodiment as shown in FIG. 1, in particular, with regard to the length measurement point registration and memory unit. Namely, in the present embodiment instead of the visual field positional deviation amount (dxm, dym) the history of the after-correction displacement target position (xmt, ymt) is stored for every length measurement point.

Figure 23:
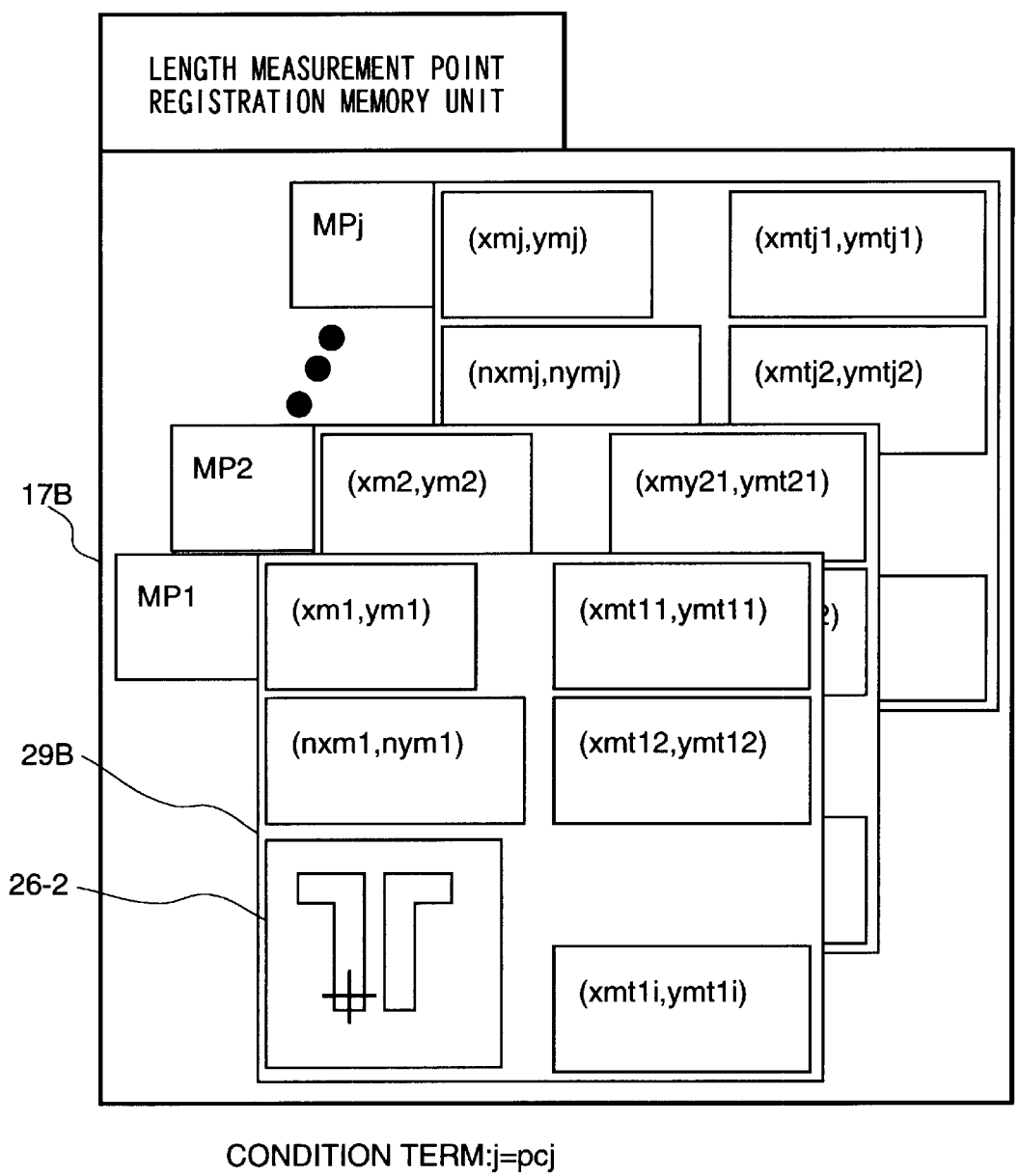
FIG. 23 is a diagram showing an example of length measurement point registration and memory unit in FIG. 1.

FIG. 23 shows an example of length measurement point registration and memory units. In the length measurement point registration and storage unit 17B, MP1, MP2 . . . , MPj of which number corresponds to that of the length measurement points and information for respective length measurement points which is necessary for performing an automatic observation are registered. For example, with regard to MP1 an observation point on the wafer 21 is displaced to a certain chip including MP1, the observation position is specifically designated on the SEM image by the pointing pen 27 and the determined observation position is converted into an in-chip coordinate value and is registered. Namely, the SEM control unit 6 determines the position of a portion desired to be observed after converting the position into in-chip coordinate value (xm, ym) of the position designated by the pointing pen 27 from sample stage coordinate value (xst, yxt) and chip allocation (nx, ny) at the moment. The thus determined in-chip coordinate value (xm, ym) and chip allocation (nx, ny) are registered and stored together with the image of the observation portion used for picture image collation as shown in FIG. 23. The same is true with regard to MP2, . . . , MPj. The scheme incorporated in the length measurement point registration and memory unit 17B is the same as that in FIG. 5.

Now, when repeating the displacement of the sample stage by a predetermined number of times to an observation position represented by in-chip coordinate value (xm, ym) and chip allocation (nx, ny), residual visual field positional deviation amounts after completing displacement of the sample stage to respective displacement target positions are measured for every time. Further, at the same time, by making use of these values as correction values the displacement target positions used at respective moments are corrected and re-determined. These after-correction displacement target position coordinate values (xmt, ymt) are registered and stored for respective length measurement points MP1, MP2, . . . , MPj depending on the observation times. For example, with regard to MP1, the visual field positional displacement amounts (dxm11, dym11), (dxm12, dym12), . . . , (dxmli, dymli) which covers displacement of i times are registered and stored. The same is turn with regard to MP2, . . . , MPj.

Figure 24:
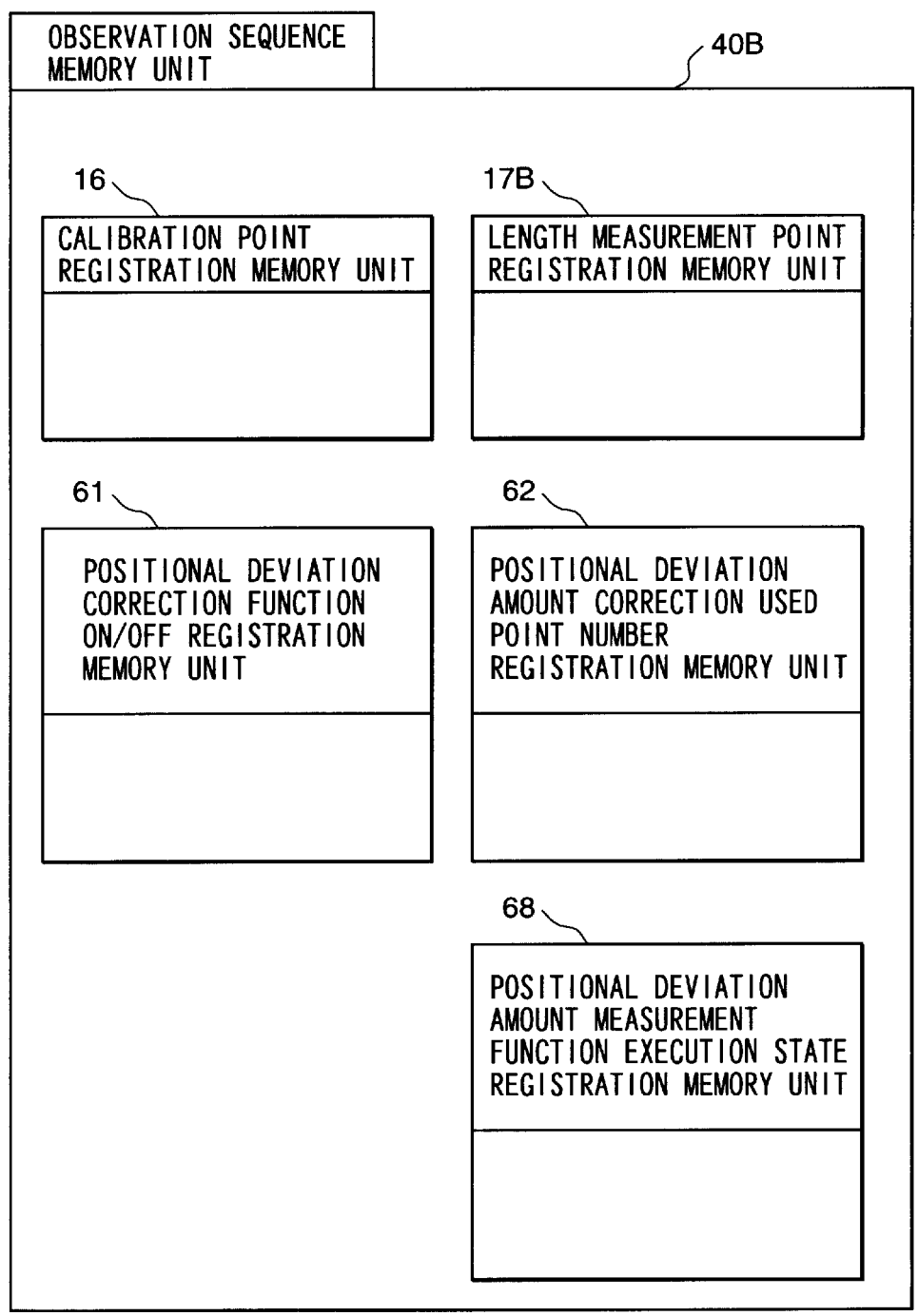
FIG. 24 is a diagram showing an example of observation sequence memory unit in FIG. 1.

Other than the manual operation of the scanning type electron microscope of the present invention, with the scanning type electron microscope of the present invention, an automatic observation can be performed through a control unit such as a computer according to a sequence (recipe) recorded in the observation sequence memory unit 40B as shown in FIG. 24. In the present invention, the observation sequence memory unit 40B is provided with a positional deviation amount measurement function ON/OFF registration and memory unit 68. In the positional deviation amount measurement function ON/OFF registration and memory unit 68 an ON/OFF state is registered as shown in FIG. 21 and switching of the ON/OFF execution state of the positional deviation amount measurement function is permitted when an automatic observation is performed by making use of the observation sequence memory unit 40B. The basic scheme of these is substantially the same as the above embodiment in which "the stored positional deviation amounts which were obtained in a predetermined interval in the past are used from a certain time point for correcting the sample stage displacement target position". Differences are, instead of the length measurement point registration and memory unit 17A, the length measurement point registration and memory unit 17B is provided and further, instead of storing the visual field positional deviation amount (dxm, dym), the after-correction displacement target position (xmt, ymt) is stored therein.

Further, the scheme used for determining the length measurement point position through the picture image collation is the same as the above embodiment as shown in FIG. 9. In the same manner as above, the displacement target position is corrected by making use of the visual field positional deviation amount determined according to the method of the present embodiment.

The above functions can be realized in softwares which drive the SEM control unit 6 for the main body of scanning type electron microscope. Accordingly, the present invention includes a variety of control boards other than the physical control board as shown in FIG. 1.

Figure 25:
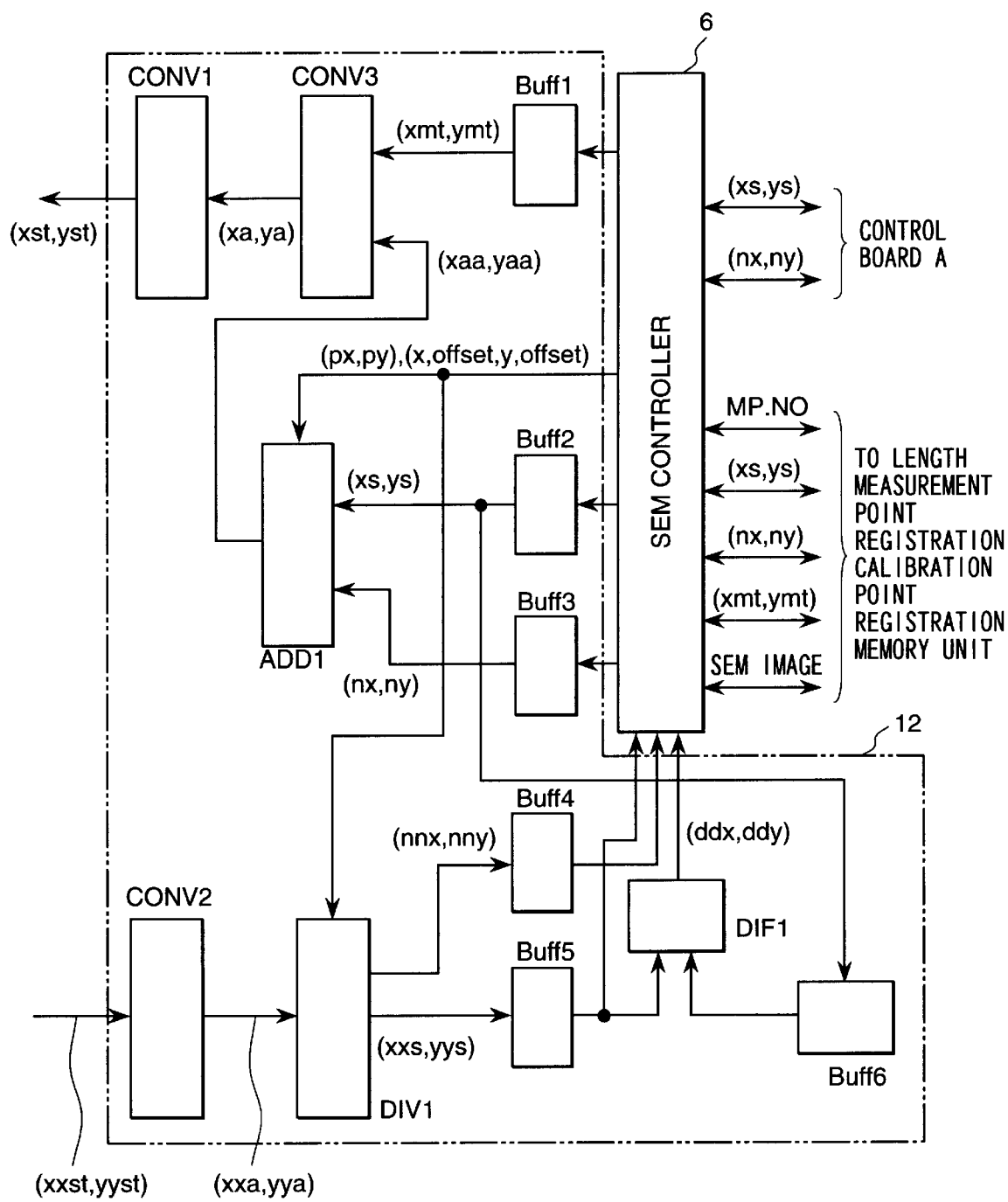
FIG. 25 is a diagram showing an arrangement of coordinate value conversion between stage coordinate and designation coordinate in FIG. 1.

FIG. 25 shows an arrangement of the coordinate value conversion between stage coordinate Xst-Yst and designation coordinate Xa-Ya.

The inside of two dotted chain line shows the structure of the coordinate value convertor 12.

The SEM control unit 6 receives signals (xs, ys), (nx, ny) designating an observation position from the control board A 7, and MP.NO representing length measurement point number NO., (xs, ys), (nx, ny) representing the observation position, (dx, dy) representing a visual field deviation until the present observation at the concerned position and SEM picture image used for identifying the length measurement point position from the length measurement point registration and memory unit 17B. These values are outputted from the SEM control unit 6, in that in the opposite direction as above, depending on necessity, for example when these values are required to be displayed on a display board and when these values are required to be registered and stored.

The SEM control unit 6 receives these data and outputs for the first time (xs, ys), (nx, ny) representing the observation position via Buff 2 and Buff 3 to ADD 1. The ADD 1 outputs a provisional designation coordinate value (xaa, yaa) based on a pitch (px, py) representing a chip design information and offset amount (xoffset, yoffset). The after-correction displacement (xmt, ymt) outputted via Buff 1 is converted by CONV 3 together with the above provisional designation coordinate value (xaa, yaa) to form a designation coordinate value (xa, ya). The designation coordinate value (xa, ya) is converted in CONV 1 into a stage coordinate value (xst, yst) and is outputted to the sample stage control unit 5.

The above series of flow shows an operation sequence when designating the coordinate value of the observation position from the SEM control unit 6 to the stage control unit 5. Herein, it is required to return in opposite direction the stage coordinate value read from the linear scale 24 to the side of the SEM control unit 6, in which stage coordinate value (xxst, yyst) representing the read coordinate value of the linear scale 24 is at first converted by CONV 2 into a designation coordinate value (xxa, yya). Like the ADD 1, DIV 1 receives the pitch (px, py) representing the chip design information and offset amount (xoffset, yoffset) from the SEM control unit 6 and converts the current sample stage position (xxa, yya) into one expressed by the chip alignment (nnx, nny) and the in-chip coordinate value (xxs, yys) based on the received values. The in-chip coordinate value (xxs, yys) is used to calculate a difference (ddx, ddy) in DIF 1 from the coordinate value (xs, ys) with regard to the observation position received at Buff 6 and being designated from the SEM control unit 6 to the stage control unit 5. The difference (ddx, ddy) represents a distance of actually caused positional deviation on the observation visual field from the designated observation position. Herein, the SEM control unit 6 performs a correction for the displacement target position used at the moment by making use of the visual field positional deviation amount (ddx, ddy) and determines a new after-correction displacement target position (xmt, ymt). Thus obtained (xmt, ymt), (xxs, yys) and (nnx, nny) are processed to be registered and stored such as in the length measurement point registration and memory unit 17A and the calibration point registration and memory unit 16.

Now, the operation sequence in the present embodiment will be explained. FIG. 1 shows a condition in which once a wafer is actually mounted on a sample stage. The positional relationship between stage coordinate Xst-Yst and designation coordinate Xa-Ya which is temporarily fixed at this moment is used as a reference position. Thereafter, the coordinate value (Xa, Ya) representing a position to be observed is converted to the coordinate value (Xst, Yst) representing actual displacement distance of the stage. The control device for the scanning type electron microscope virtually registers the plurality of chips in a grid shape on the wafer according to the coordinate at this instance while framing such as the chip size, allocation and rotation direction in the wafer plane in a square chip outer configuration in a relationship based on the chip design data. In FIG. 1, 3×3 chips are aligned. Among these chips represented by grids two chips include characteristic points 4a and 4b (as illustrated by cross marks) used for position definition which are suitable for performing calibration. Further, another grid includes a point 4c (as illustrated by a cross mark) representing a pattern position to be observed.

Thereafter, with the in-chip coordinate Xt-Yt each being defined with reference to respective grids, the coordinate value of the position of observation portion (pattern) within a chip is expressed. In FIG. 1 the coordinate value is expressed as (Xs, Ys). When observing the same observation portion but of a different chip, the coordinate value of the observation position is determined while taking into account of an offset corresponding to a chip alignment pitch for the in-chip coordinate value.

At first, the characteristic points are registered for coordinate calibration between stage coordinate Xst-Yst and designation coordinate Xa-Ya. Through manipulation of the track ball 13, a characteristic AP 1 (such as a part on a chip pattern or a tag used for an exposure position matching) of a first sample 4a is displaced to the center of the visual field of the microscope, and the registration switch for the coordinate calibration point AP 1 is operated. Thereby, the stage control unit 6 is placed under a condition of waiting for an input of designation coordinate value from the control board A 7. Subsequently, the positions of the characteristic points used for the coordinate calibration are designated on the SEM picture image 9 of the control board A 7 by the pointing pen 27. The control board A 7 outputs a coordinate value based on the coordinate Xm-Ym in the visual field reproduced on the SEM picture image 9. In this instance the coordinate Xm-Ym has the origin, for example, at the center of the visual field which coincides or corresponds to the stop position of the sample stage. The SEM control unit 6 determines a registration position (xch1, ych1) of the location use coordinate calibration point AP 1 through calculation of the coordinate value (xm1, Ym1) and read value (xL1, yL1) of the linear scale 24 representing the position of the sample stage and stores the same. The above calculation is, for example, performed by adding the both values as expressed by the following equations (4);

$$\left.\begin{array}{l}xch1 = xm1 + xL1 \\ ych1 = ym1 + yL1\end{array}\right\} \quad (4)$$

Other than the processing with regard to these coordinate positions, the SEM picture image at this moment is at the same time recorded and is registered while relating AP 1 at this moment with the picture image. The manner is shown in connection with the calibration point registration and memory unit 16 in FIG. 4. For example, AP 1 representing the registered calibration point No.1 is defined by in-chip coordinate value (xa1, ya1) of the observation point and chip alignment (nxa1, nya1). Further, the pattern position for the picture image collation is designated by a cross mark in the registered SEM picture image. Thereby, for the subsequent observation the control unit for the scanning type electron microscope determines the position coordinate value (xst, yst) to which the sample stage is to be automatically displaced from the in-chip coordinate value (xa, ya) of the characteristic point position and the chip alignment position (nxa, nya) registered in advance and further performs an automatic identification of the coordinate calibration point through picture image collation with a calibration point portion image 26-1 which is stored while relating to the determined portion. Subsequently, in the like manner as above, the characteristic position AP 2 of a second sample 4b is registered, and (xch2, ych2) is stored. Further, like the first characteristic point AP 1 the SEM image is recorded.

Herein, the wafer 21 representing a sample is actually displaced manually, for example, by means of the track ball 13 while mounting the same on the sample stage 1 and observing through the scanning type electron microscope to designate manually with the pointing pen 27 the position of a portion desired to be observed on the actual sample. Further, when the registration switch of the length measurement point MP in the control board B 15 is pressed, the SEM control unit 6 determines the position of a portion desired to be observed after converting the position into in-chip coordinate value (xs, ys) from sample stage coordinate value (xst, yst) and chip allocation (nx, ny) at the moment, and stores together with the SEM picture image of the observation portion while being related therewith. The manner is shown in connection with the length measurement point registration and memory unit 17A in FIG. 5. For example, MP 1 representing the registered length measurement point No.1 is defined by in-chip coordinate value (xm1, ym1) of the observation point and chip alignment (nxm1, nym1). Further, the pattern position for the length measurement is designated by a cross mark in the registered SEM picture image. Thereby, for the subsequent observation the SEM control unit 6 determines the coordinate value (xst, yst) to which the sample stage is to be automatically displaced from the in-chip coordinate value (xs, ys) of the observation portion position and the chip alignment position (nxa, nya) registered in advance and further performs an automatic identification of the observation portion through picture image collation with an observation portion image 26-2 which is stored while relating to the determined portion. After completing the registration of the above characteristic points, when subsequently mounting a wafer on the sample stage the coordinate calibration is performed by collating the registered positions of the characteristic point which enhances positional accuracy in coordinate designation.

Subsequently, the process moves to an observation stage. At first, a coordinate calibration between stage coordinate Xst-Yst and designation coordinate Xa-Ya is performed. Through manipulation of the track ball 13, a characteristic point AP 1 of a first sample 4a is displaced to the center of the visual field of the microscope, and the registration switch for the coordinate calibration point AP 1 is operated. Thereby, the stage control unit 6 is placed under a condition of waiting for an input from the control board A 7. Subsequently, the positions of the characteristic points used for the coordinate calibration are designated on the SEM picture image 9 of the control board A 7 by the pointing pen 27. The control board A 7 outputs a coordinate value based on the coordinate Xm-Ym in the visual field reproduced on the SEM picture image 9. In this instance the coordinate Xm-Ym has the origin, for example, at the center of the visual field which coincides or corresponds to the stop position of the sample stage. The SEM control unit 6 determines a position (x1, y1) of the location use coordinate calibration point AP 1 through calculation of the coordinate value (xm1, Ym1) and read value (xL1, yL1) of the linear scale 24 representing the position of the sample stage in the same manner as in the above registration.

With regard to the second characteristic point AP 2, the coordinate position (x2, y2) is determined in the same manner as in AP 1.

After determining (x1, y1) and (x2, y2) as has been explained above, these coordinate values are compared and calculated with the positions (xch1, ych1) and (xch2, ych2) at the time of registration, thereby, the coordinate calibration between coordinate Xa-Ya on the coordinate designation means and sample stage coordinate Xst-Yst is performed. The coordinate calibration can be performed in the same manner as disclosed in the prior art U.S. Pat. No. 4,814,682 as referred to above.

The SEM control unit 6, which has received chip alignment (nx, ny), in chip coordinate value (xs, ys) and visual field deviation amount (dx, dy) which are stored in the length measurement point registration and memory unit 17A, determines designation coordinate value (xa, ya) of a pattern portion to be observed and length-measured and outputs the same to the coordinate value conversion unit 12, wherein a conversion according to the following equations (5) is performed;

$$\left.\begin{array}{l} dx = fsx(dxm(1), dxm(2), \ldots) \\ dy = fsy(dym(1), dym(2), \ldots) \end{array}\right\} \quad (5)$$

Practically, it is necessary to limit the memory capacity to a certain extent, therefore, it is actually impossible to hold and use unlimited number of visual field deviation amounts. Accordingly, the following equations (6) are used for the conversion.

$$\left.\begin{array}{l} dx = fsx(dxm(1), dxm(2), \ldots dxm(j)) \\ dy = fsy(dym(1), dym(2), \ldots dym(j)) \end{array}\right\} \quad (6)$$

Wherein, fsx and fsy are functions representing a statistical processing method according to the present invention. Further, j=mpj (wherein, mjp: registered valid data number for positional deviation correction).

Herein, one example of simply realized methods among the statistical processing methods is a method of averaging a predetermined number of results according to the following equations (7).

$$\left.\begin{array}{l} dx = (dxm(1) + dxm(2) + \ldots + dxm(j))/j \\ dy = (dym(1) + dym(2) + \ldots + dym(j))/j \end{array}\right\} \quad (7)$$

Wherein, j=mpj (wherein, mjp: registered valid data number for positional deviation correction).

Further, another example of statistical processing methods is a method of weighted-averaging putting weight on the latest result with regard to a predetermined number of results according to the following equations (8).

$$\left.\begin{array}{l} dx = (D1 \cdot dxm(1) + D2 \cdot dxm(2) + \ldots + Dj \cdot dxm(j))/j \\ dy = (D1 \cdot dym(1) + D2 \cdot dym(2) + \ldots + Dj \cdot dym(j))/j \end{array}\right\} \quad (8)$$

Wherein, D1<D2< . . . <Dj and (D1+D2+ . . . +Dj)/j=1.

Further, j=mpj (wherein, mjp: registered valid data number for positional deviation correction).

Still further, dxm(j) is the latest data, the second latest data is dxm(j−1), . . . , dxm(2) is the second oldest data and dxm(1) is the oldest data. The same is true with regard to dym(j), dym(j−1), . . . , dym(2), dym(1).

On the other hand, there is still another embodiment in which after every displacement completion of the sample stage the measurement result of the visual field positional deviation amount is reflected every time on the displacement target position to determine an after-correction displacement target position and to store the same, and which is repeatedly used when being displaced subsequently to the same portion or the corresponding portion. The basic ideas of the present embodiment such as the method of designating a position desired to be observed by making use of designation coordinate Xa-Ya, the method of performing coordinate calibration between designation coordinate Xa-Ya and stage coordinate Xst-Yst and the determination of (nxm, nym) and (xm, ym) representing length measurement point position and registration thereof into the length measurement point registration and memory unit 17B are substantially the same as in the previous embodiment. A displacement target position (xmt (j+1), ymt (j+1)) for the subsequent observation is determined from measured visual field positional deviation amount (dxm, dym) according to the following equations (9).

$$\left.\begin{array}{l} xmt(j+1) = xmt(j) - dxm(j) \\ ymt(j+1) = ymt(j) - dym(j) \end{array}\right\} \quad (9)$$

Through repeating the above calculation after every displacement completion of the sample stage to the observation position, the displacement target positions are time sequentially determined. Further, the determined results are automatically stored in the length measurement point registration and memory unit 17B.

A displacement target position at that moment is determined after every displacement completion of the sample stage from a visual field positional deviation amount as has been explained above, and further, for the subsequent displacement to the same or a corresponding observation point a plurality of displacement target positions which were determined time sequentially in the past and were stored are likely read out from the length measurement point registration and memory unit 17B, and the read data are subjected to a statistical processing to determine a new displacement target position to which the sample stage is displaced, accordingly, a stop position accuracy of the sample stage can stably be obtained.

Namely, the SEM control unit 6, which has received chip alignment (nx, ny), in-chip coordinate value (xs, ys) and displacement target position (xmt, ymt) which are stored in the length measurement point registration and memory unit 17B, determines designation coordinate value (xa, ya) of a pattern portion to be observed and length-measured and outputs the same to the coordinate value conversion unit 12, wherein a conversion according to the following equations (10) is performed;

$$\left.\begin{array}{l} xmt = fssx(xmt(S-1), xmt(S-2), \ldots) \\ ymt = fssy(ymt(S-1), ymt(S-2), \ldots) \end{array}\right\} \quad (10)$$

Wherein, S represents a time point immediately before the sample stage displacement for the subsequent observation, and the time traces back to the past as S−1, S−2, . . . Practically, it is necessary to limit the memory capacity to a certain extent, therefore, it is actually impossible to hold and use unlimited number of displacement target positions. Accordingly, the following equations (11) are used for the conversion.

$$xmt = fssx(xmt(S-1), xmt(S-2), \ldots xmt(S-j)) \atop ymt = fssy(ymt(S-1), ymt(S-2), \ldots ymt(S-j))\} \quad (11)$$

Wherein, fssx and fssy are functions representing a statistical processing method according to the present invention. Further, j=mpj (wherein, mjp: registered valid data number for positional deviation correction).

Herein, one example of simply realized methods among the statistical processing methods is a method of averaging a predetermined number of results according to the following equations (12).

$$xmt = (xmt(S-1) + xmt(S-2) + \ldots + xmt(S-j))/j \atop ymt = (ymt(S-1) + ymt(S-2) + \ldots + ymt(S-j))/j\} \quad (12)$$

Wherein, j=mpj (wherein, mjp: registered valid data number for positional deviation correction).

Further, another example of statistical processing methods is a method of weighted-averaging putting weight on the latest result with regard to a predetermined number of results according to the following equations (13).

$$xmt - (D1 \cdot xmt(S-1) + D2 \cdot xmt(S-2) + \ldots + Dj \cdot xmt(S-j))/j \atop ymt - (D1 \cdot ymt(S-1) + D2 \cdot ymt(S-2) + \ldots + Dj \cdot ymt(S-j))/j\} \quad (13)$$

Wherein, D1<D2< . . . <Dj and (D1+D2+ . . . +Dj)/j=1.

Further, j=mpj (wherein, mjp: registered valid data number for positional deviation correction).

Still further, xmt(S−1) is the latest data, the second latest data is xmt(S−2), . . . , xmt(S−j+1) is the second oldest data and xmt(S−j) is the oldest data. The same is true with regard to ymt(S−1), ymt(S−2), . . . , ymt(S−j+1), ymt(S−j).

Thereafter, the coordinate value conversion unit 12 converts the determined displacement target position (xmt, ymt) into stage coordinate value (xst, yst) representing a position where the sample stage 1 is actually to be displaced and outputs the same to the stage control unit 5. Then, the stage control unit 5 drives the motors 2 and 3 each displaces the sample stage 1 in X and Y directions until the inputted coordinate value coincides with the coordinate value (xL, yL) indicated by the linear scale 24 or with the corresponding positional coordinate value. After completing displacement of the sample stage to the predetermined position, a predetermined operation such as observation and length measurement is performed by making use of an image of the scanning type electron microscope and after completing the operation, displacement to the subsequent stage observation point is started.

In the methods as explained above, when a wafer is remounted for the subsequent observation after completing registration of the characteristic points, the characteristic points are manually designated by making use of such as the pointing pen 27. However, such designation can be performed through automatic recognition by a picture image collation of a pattern configuration near the characteristic points reproduced on the SEM picture image with the SEM picture image of the characteristic points which were stored at the time of characteristic point registration while relating to the positions. Thereby, in the course of an automatic observation by an microscope, the automatic coordinate calibration, automatic observation position extraction and automatic length measurement can be performed quickly and correctly. Further, the automatic recognition through the picture image collation can likely be applied to the designation of observation position.

Figure 19:
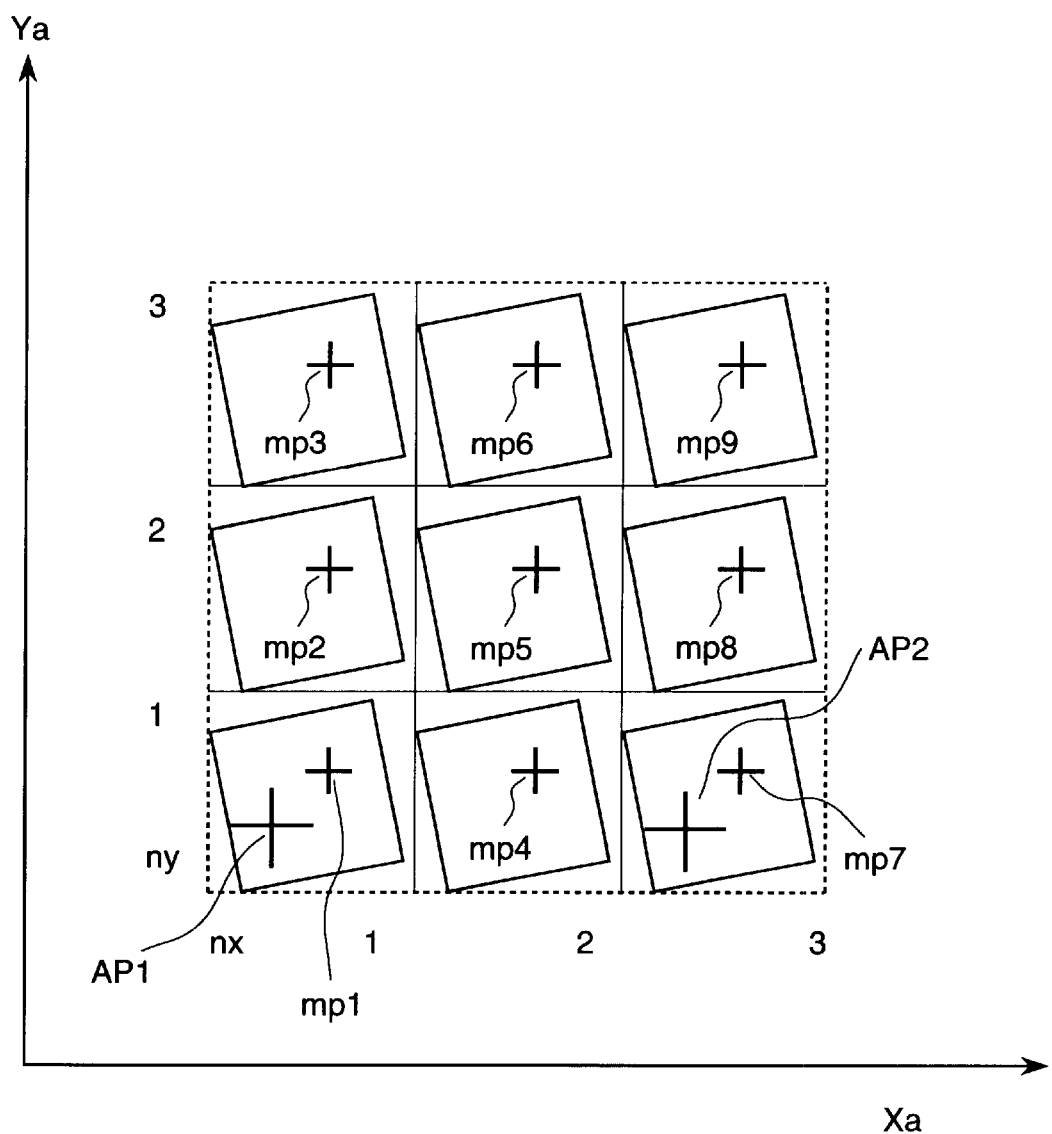
FIG. 19 is a diagram showing a state in which all of the actual chips are inclined with a certain angle with respect to design data grids.
Figure 20:
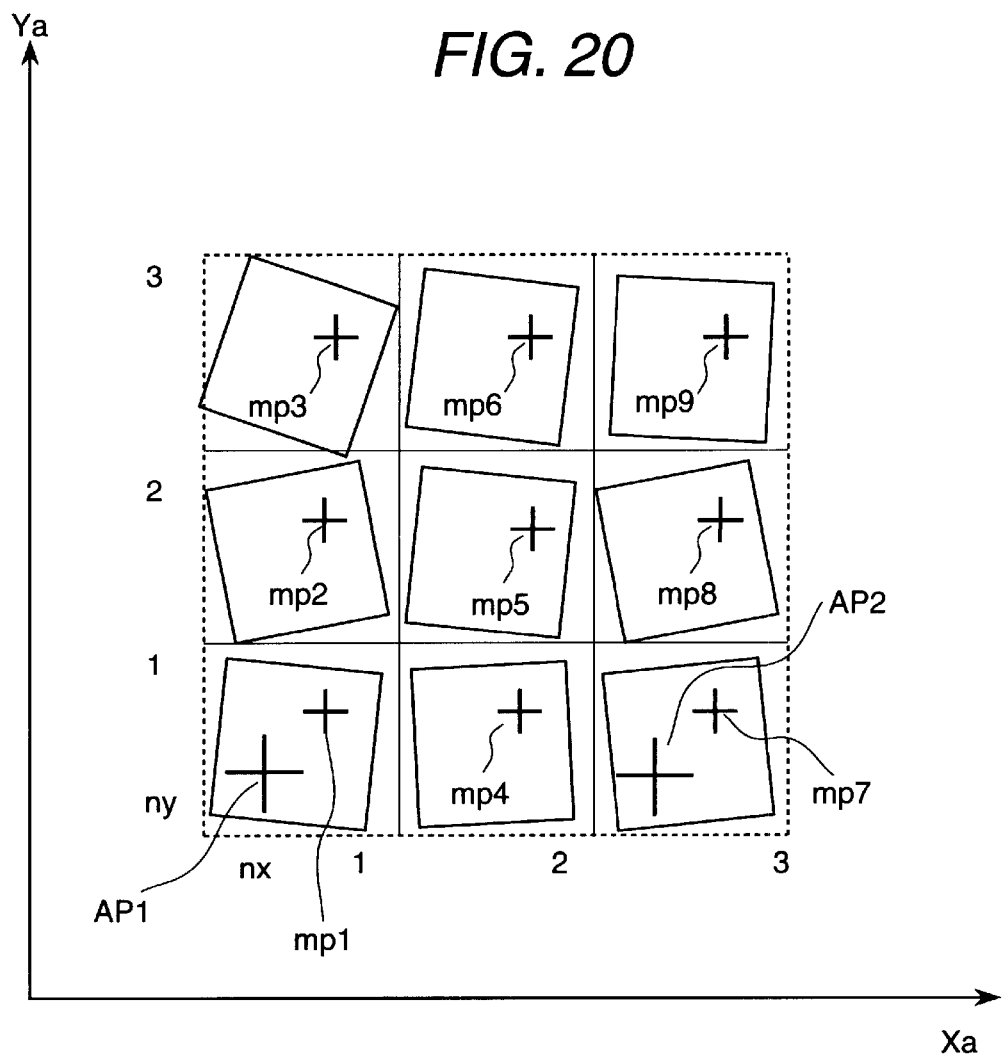
FIG. 20 is a diagram showing a state in which respective actual chips are individually inclined with respect to design data grids.

Through the use of the above explained present invention, even in a case, such as shown in FIGS. 19 and 20, when all of the actual chips as illustrated by solid lines are inclined with a certain angle in respective grids according to the design data as illustrated by broken lines, and when actual chips as illustrated in solid lines are individually inclined with respect to the grids according to the design data as illustrated by broken lines and the positions of the length measurement points mp1~mp9 are inclined together with the respective chips and deviate from their ideal positions, the position of the length measurement points mp1~mp9 can be correctly captured within the visual field of the scanning type electron microscope.

Figure 30:
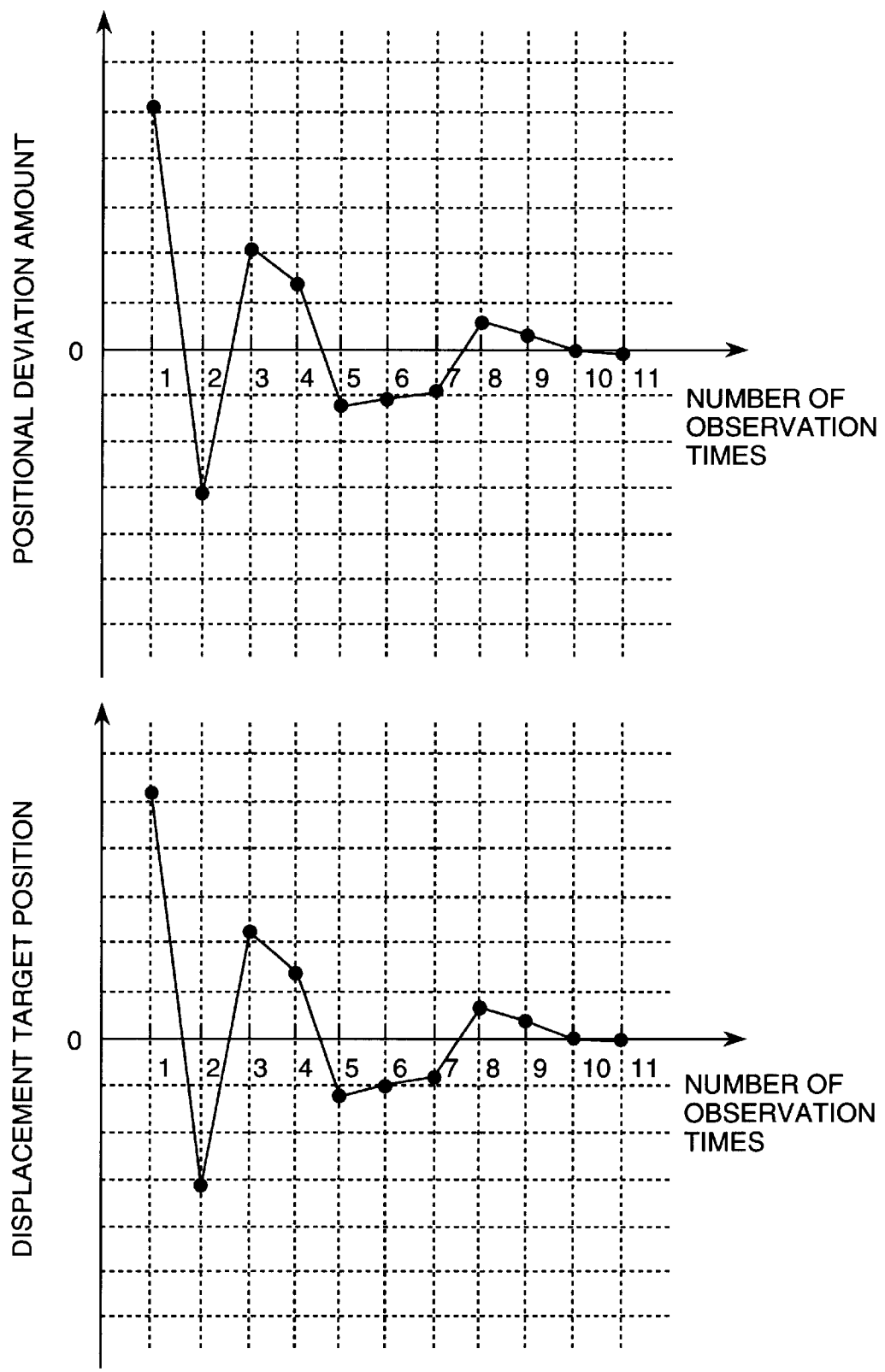
FIG. 30 is a diagram showing a manner in which positional deviation amount gradually converges as the number of observation times increases.

Through the practice of the present invention as has been explained above, the positional deviation amount gradually converges near to zero as the number of observation times increases as shown in FIG. 30. Accordingly, for an electron microscope which is suitable for an application in which the samples are repeatedly observed, a further accurate positioning operation of the sample stage can be realized.

In the above embodiments, a possible instance when an automatic observation according to a same observation sequence is required to be performed in different devices is not taken into account. However, it is frequently required, while preparing a plurality of observation devices of same type, to perform an automatic observation according to the same observation sequence. The present invention can likely be applied to such requirement, if only the record of observation sequence including calibration point record and length measurement point record is exchanged.

Between a plurality of scanning type electron microscopes, it is frequently caused variation in production precision of the sample stages. It is always necessary to clarify to which device the record detection result of positional deviation amount belongs. In the present invention, a device identification mark such as device manufacturer's serial number is registered together with the detection result of positional deviation amount (dxm, dym) in the observation sequence registration and memory unit 40A (40B).

Figure 13:
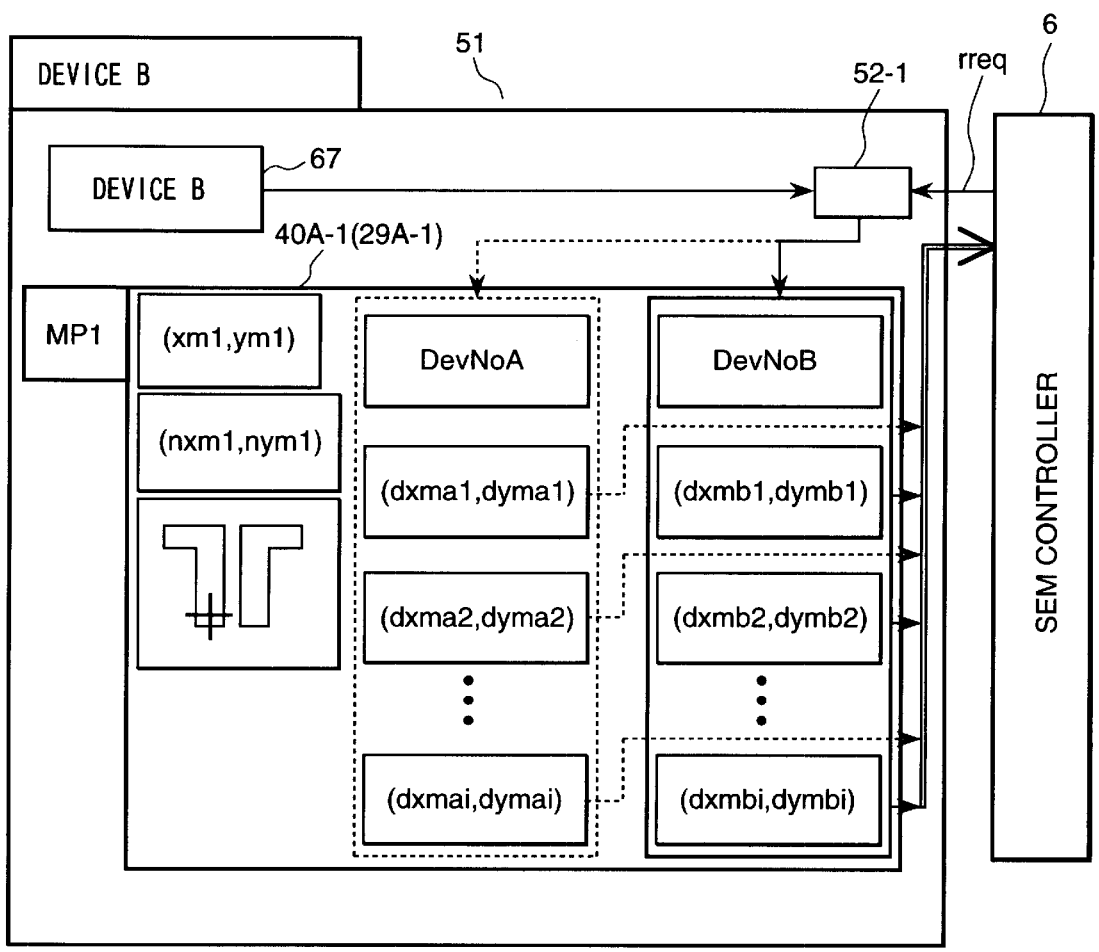
FIG. 13 is a diagram showing a read state from the observation sequence memory unit in device B.

FIG. 13 shows a block diagram wherein a positional deviation amount (dxm, dym) is already stored in the observation sequence registration memory unit 40A while relating to the device identification mark such as device manufacturer's serial number and the same are read into the SEM control unit 6 and are utilized as correction data for the stage position after finding out chip alignment (nxm1, nym1) and in-chip coordinate value (xm1, ym1) of displacement target position of the sample stage for the subsequent observation position and prior to starting the sample stage displacement.

When a device identification unit 52-1 receives from the SEM control unit 6 a read request signal rreq of positional deviation correction data, the device identification unit 52-1 reads a device identification mark "B" from a device identification memory unit 67 which is individually provided for each scanning type electron microscope B 51 and transmits the read mark to the observation sequence registration and memory unit 40A-1. The observation sequence registration and memory unit 40A-1 outputs to the SEM control unit 6 the positional deviation correction data (dxmb1, dymb1), (dxmb2, dymb2), . . . , (dxmbi, dymbi) which are related to the device number DevNoB to perform the positional deviation correction, representing the characteristic of the present invention, which is indicated by solid line arrows. When, for example, a device identification mark "A" is outputted from the device identification memory unit 67, the positional deviation correction data (dxma1, dyma1), (dxma2, dyma2), . . . , (dxmai, dymai) which are related to the device number DevNoA are outputted to the SEM control unit 6 as indicated by broken line arrows.

Figure 14:
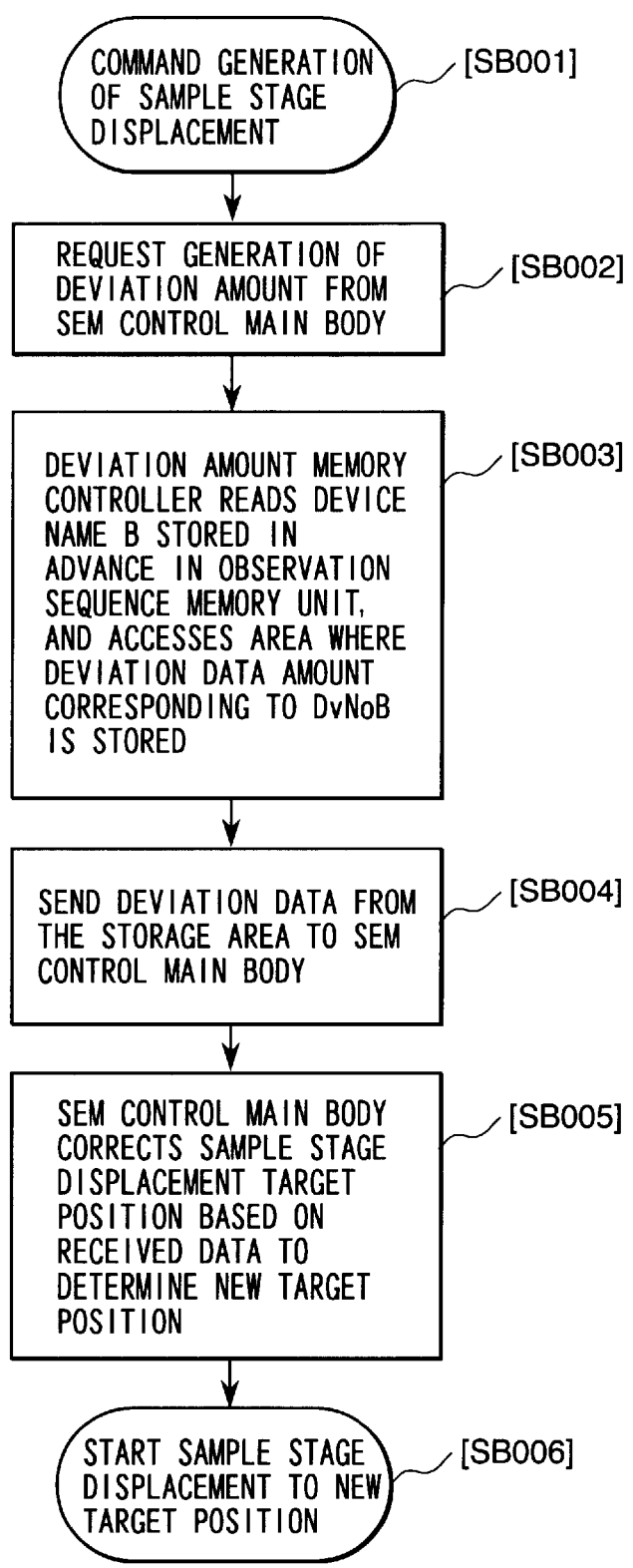
FIG. 14 is a flow chart showing an example of operation sequence performed in FIG. 1.

The above processing flow is shown in FIG. 14 flow chart.

Step SB 001: Command generation of the sample stage displacement

Step SB 002: Request generation of deviation amount from the SEM controller main body Step SB 003: A deviation amount memory controller reads device name B which is stored in advance in the observation sequence memory unit, and accesses an area where the deviation amount data corresponding to DvNoB Step SB 004: The deviation amount data are sent from the storage area to the SEM controller main body Step SB 005: The SEM controller main body corrects sample stage displacement target position based on the received data to form a new target position Step SB 006: Start displacement of the sample stage to the new target position.

Figure 15:
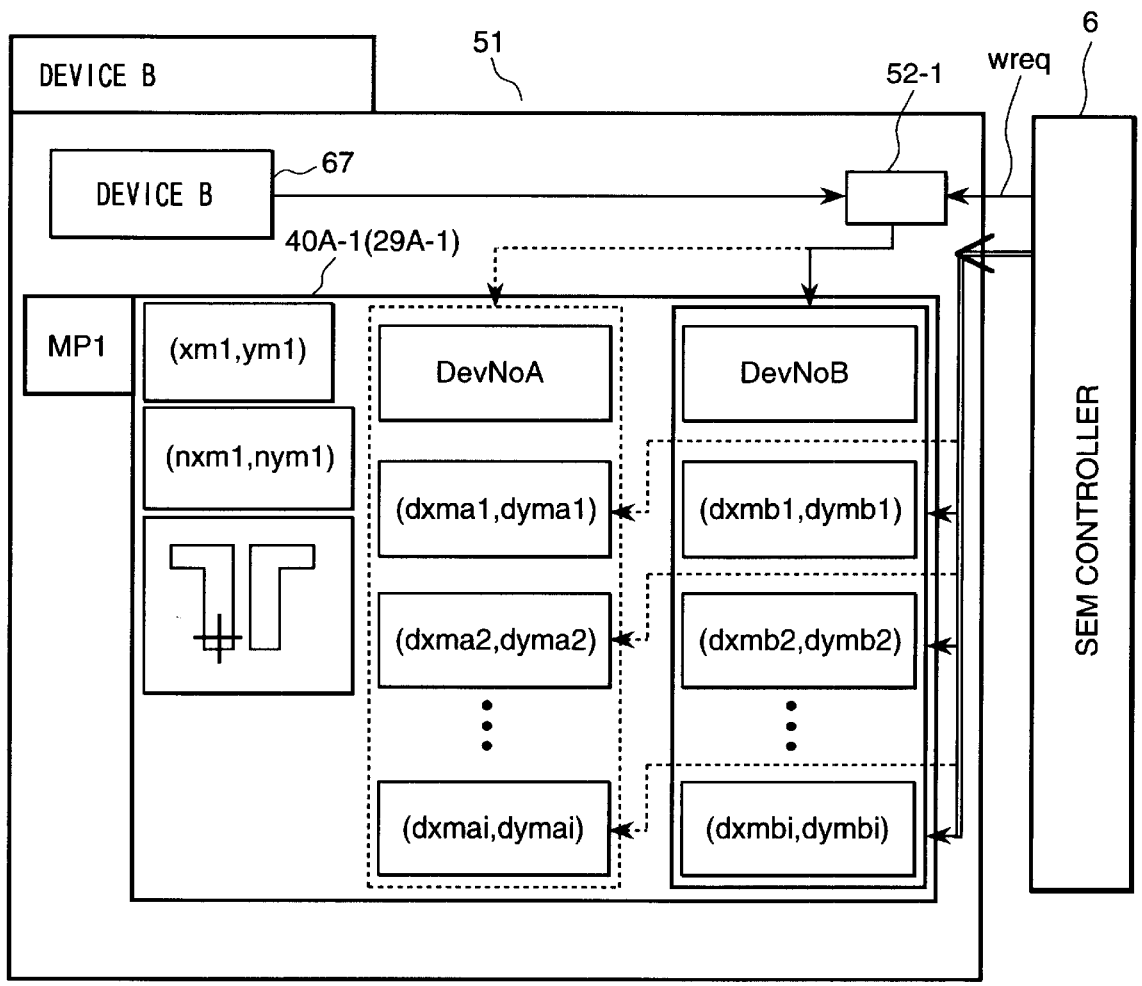
FIG. 15 is a diagram showing a write state to the observation sequence memory unit in device B.

FIG. 15 shows a block diagram wherein a measured positional deviation amount (dxm, dym) is stored in the observation sequence registration memory unit 40A while relating to the device identification mark such as device manufacturer's serial number after the sample stage has been stopped at chip alignment (nxm1, nym1) and in-chip coordinate value (xm1, ym1) of displacement target position of the sample stage for the observation position.

When a device identification unit 52-1 receives from the SEM control unit 6 a write request signal wreq of positional deviation correction data, the device identification unit 52-1 reads a device identification mark "B" from a device identification memory unit 67 which is individually provided for each scanning type electron microscope B 51 and transmits the read mark to the observation sequence registration and memory unit 40A-1. The observation sequence registration and memory unit 40A-1 successively stores positional deviation amounts outputted from the SEM control unit 6 at the positional deviation correction data storage positions (dxmb1, dymb1), (dxmb2, dymb2), . . . , (dxmbi, dymbi) which are related to the device number DevNoB, which is indicated by solid line arrows. When, for example, a device identification mark "A" is outputted from the device identification memory unit 67, the SEM control unit 6 outputs the positional deviation amount to the positional deviation correction data storage positions (dxma1, dyma1), (dxma2, dyma2), . . . , (dxmai, dymai) which are related to the device number DevNoA as indicated by broken line arrows.

Figure 16:
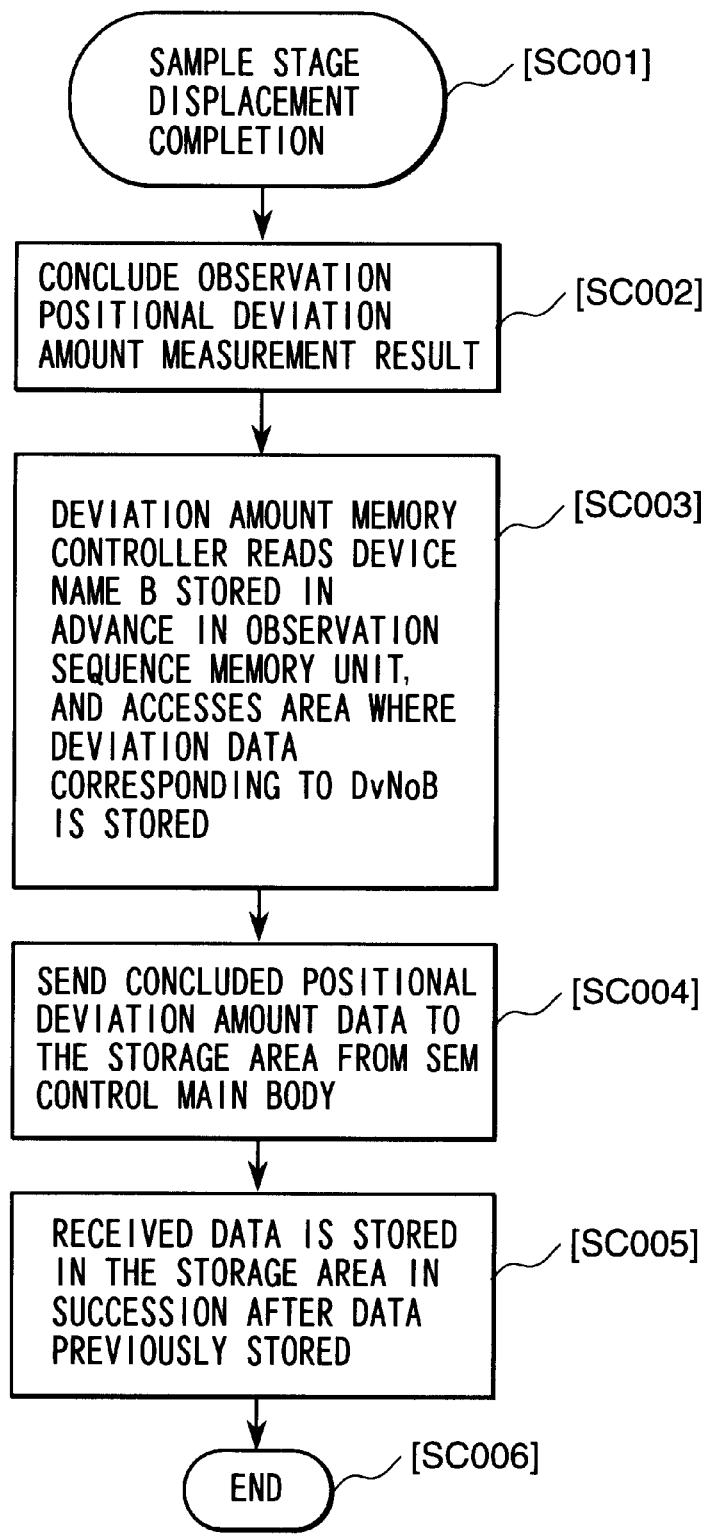
FIG. 16 is a flow chart of an example of operation sequence performing in FIG. 1.

The above processing flow is shown in FIG. 16 flow chart.

Step SC 001: Complete displacement of the sample stage displacement

Step SC 002: Conclude measurement result of the observation position deviation amount Step SC 003: The deviation amount memory controller reads device name B which is stored in advance in the observation sequence memory unit and accesses an area where deviation amount data corresponding to DvNoB is to be stored Step SC 004: The concluded positional deviation amount data are sent from the SEM controller main body to the storage positions Step SC 005: At the storage position, the received data are successively stored following the data stored previously Step SC 006: End the processing.

As has been explained above, there is an embodiment in which after every displacement completion of the sample stage the measurement result of the visual field positional deviation amount is reflected every time on the displacement target position to determine an after-correction displacement target position and to store the same, and which is repeatedly used when being displaced subsequently to the same portion or the corresponding portion, in the this embodiment, instead of the measured visual field positional deviation amount (dxm, dym), displacement target position (xmt, ymt) which is corrected by making use of the deviation amount is dealt with.

Figure 26:
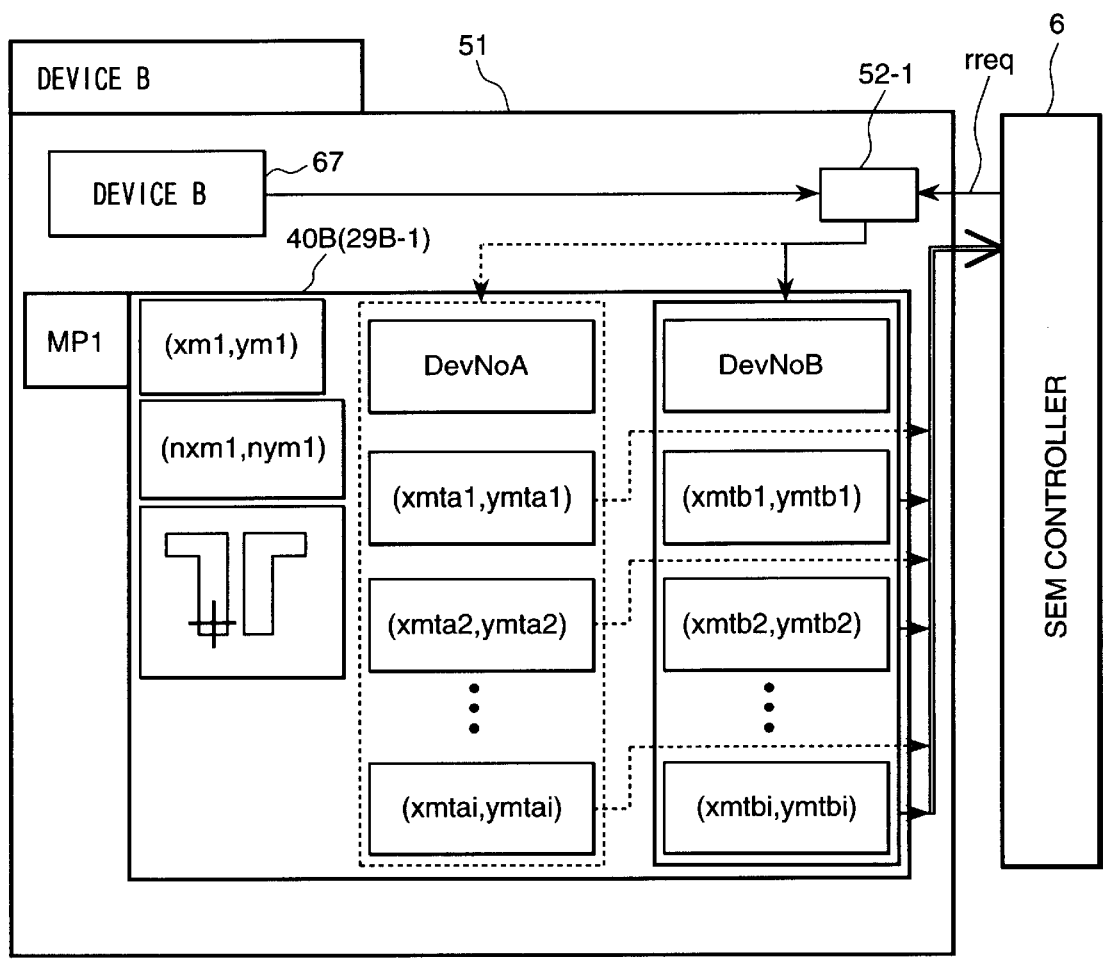
FIG. 26 is a diagram showing a read state from an observation sequence memory unit in device B.

FIG. 26 shows a block diagram wherein an after-correction displacement target position (xmt, ymt) is already stored in the observation sequence registration memory unit 40B while relating to the device identification mark such as device manufacturer's serial number and the same are read into the SEM control unit 6 and are utilized as correction data for the stage position after finding out chip alignment (nxm1, nym1) and in-chip coordinate value (xm1, ym1) of after-correction displacement target position of the sample stage for the subsequent observation position and prior to starting the sample stage displacement.

When a device identification unit 52-1 receives from the SEM control unit 6 a read request signal rreq of after-correction displacement target position data, the device identification unit 52-1 reads a device identification mark "B" from a device identification memory unit 67 which is individually provided for each scanning type electron microscope B 51 and transmits the read mark to the observation sequence registration and memory unit 40A-1. The observation sequence registration and memory unit 40A-1 outputs to the SEM control unit 6 the after-correction displacement target position data (xmtb1, ymtb1), (xmtb2, ymtb2), . . . , (xmtbi, ymtbi) which are related to the device number DevNoB to perform the positional deviation correction, representing the characteristic of the present invention, which is indicated by solid line arrows. When, for example, a device identification mark "A" is outputted from the device identification memory unit 67, the positional deviation correction data (xmta1, ymta1), (xmta2, ymta2), . . . , (xmtai, ymtai) which are related to the device number DevNoA are outputted to the SEM control unit 6 as indicated by broken line arrows.

Figure 27:
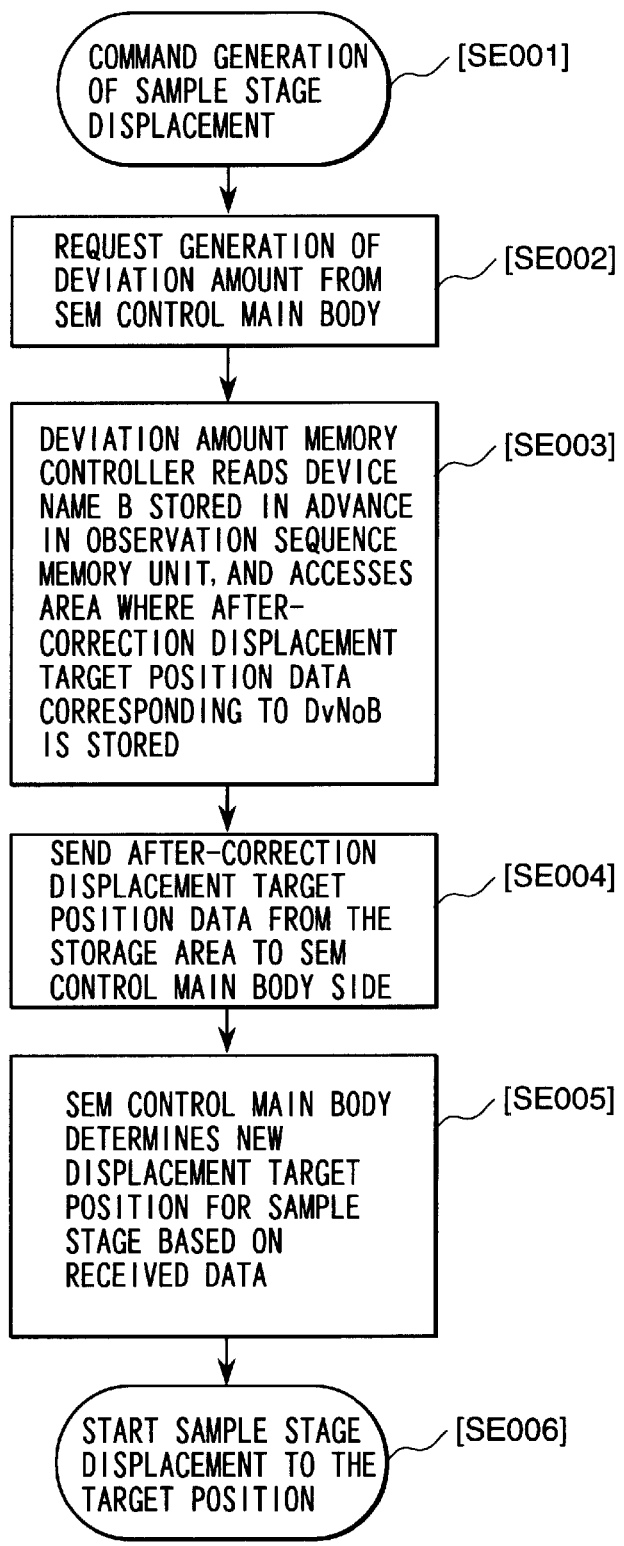
FIG. 27 is a flow chart showing an example of operation sequence performed in FIG. 1.

The above processing flow is shown in FIG. 27 flow chart.

Step SE 001: Command generation of the sample stage displacement

Step SE 002: Request generation of deviation amount from the SEM controller main body Step SE 003: A deviation amount memory controller reads device name B which is stored in advance in the observation sequence memory unit, and accesses an area where the after-correction displacement target position data corresponding to DvNoB Step SE 004: The after-correction displacement target position data are sent from the storage area to the SEM controller main body Step SE 005: The SEM controller main body corrects sample stage displacement target position based on the received data to form a new target position Step SE 006: Start displacement of the sample stage to the new target position.

Figure 28:
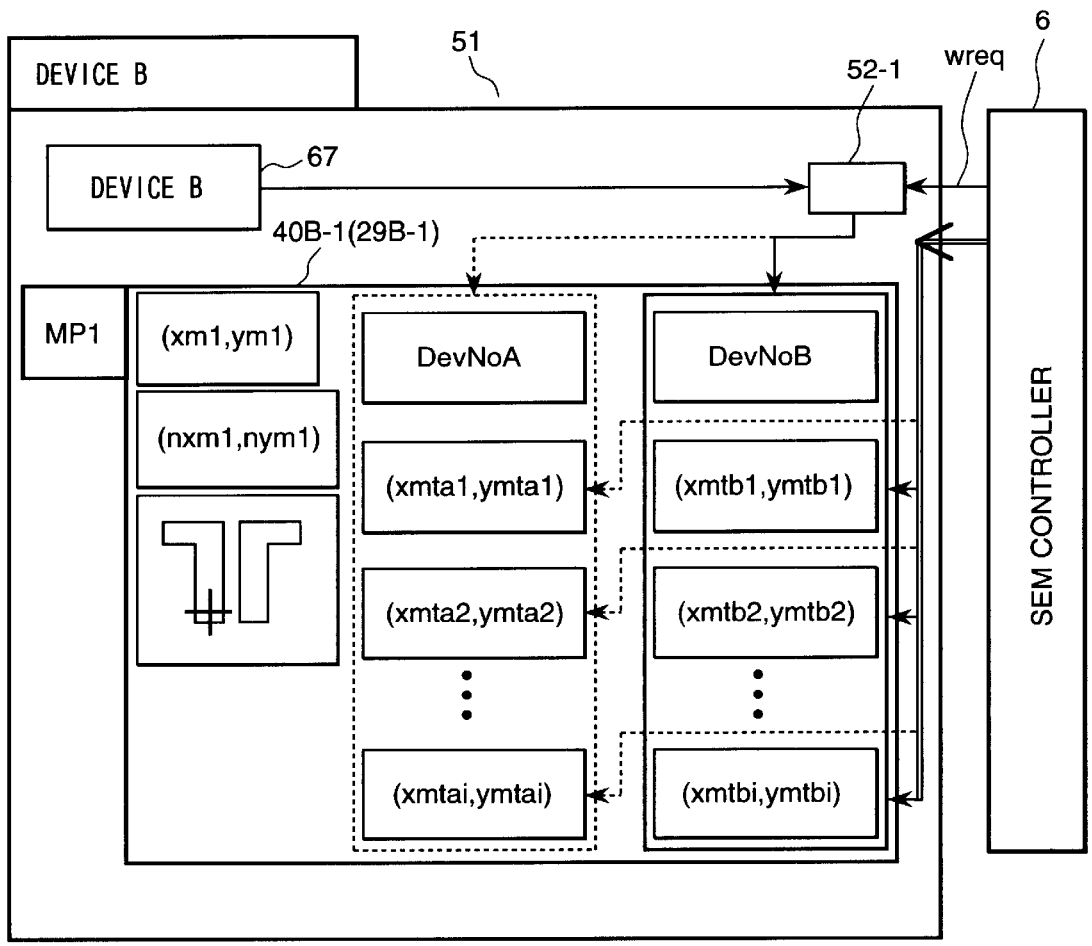
FIG. 28 is a diagram showing a write state in an observation sequence memory unit in device B.

FIG. 28 shows a block diagram wherein an after-correction displacement target position (xmt, ymt) determined from measured positional deviation amount (dxm, dym) is stored in the observation sequence registration memory unit 40B while relating to the device identification mark such as device manufacturer's serial number and after the sample stage has been stopped at chip alignment (nxm1, nym1) and in-chip coordinate value (xm1, ym1) of displacement target position of the sample stage for the observation position.

When a device identification unit 52-1 receives from the SEM control unit 6 a write request signal wreq of after-correction displacement target position data, the device identification unit 52-1 reads a device identification mark "B" from a device identification memory unit 67 which is individually provided for each scanning type electron microscope B 51 and transmits the read mark to the observation sequence registration and memory unit 40A-1. The observation sequence registration and memory unit 40A-1 successively stores after-correction displacement target position outputted from the SEM control unit 6 at the after-correction displacement target data position data storage positions (xmtb1, ymtb1), (xmtb2, ymtb2), . . . , (xmtbi, ymtbi) which are related to the device number DevNoB, which is indicated by solid line arrows. When, for example, a device identification mark "A" is outputted from the device identification memory unit 67, the SEM control unit 6 outputs the after-correction displacement target position to the after-correction displacement target position data storage positions (xmtb1, ymtb1), (xmtb2, ymtb2), . . . , (xmtbi, ymtbi) which are related to the device number DevNoA as indicated by broken line arrows.

Figure 29:
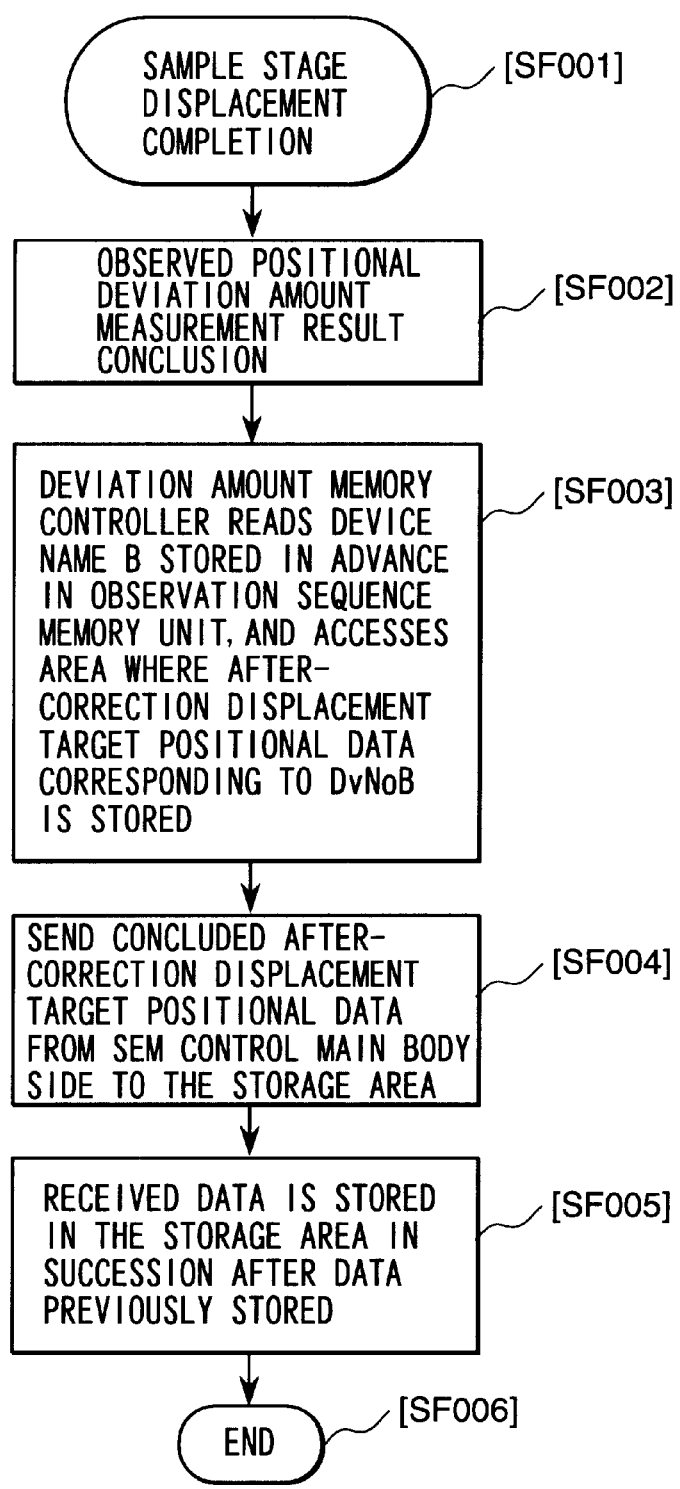
FIG. 29 is a flow chart showing an example of operation sequence performed in FIG. 1.

The above processing flow is shown in FIG. 29 flow chart.

Step SF 001: Complete displacement of the sample stage displacement

Step SF 002: Conclude measurement result of the observation position deviation amount Step SF 003: The deviation amount memory controller reads device name B which is stored in advance in the observation sequence memory unit and accesses an area where after-correction displacement target position data corresponding to DvNoB is to be stored Step SF 004: The concluded after-correction displacement target position data are sent from the SEM controller main body to the storage positions Step SF 005: At the storage position, the received data are successively stored following the data stored previously Step SF 006: End the processing.

Figure 17:
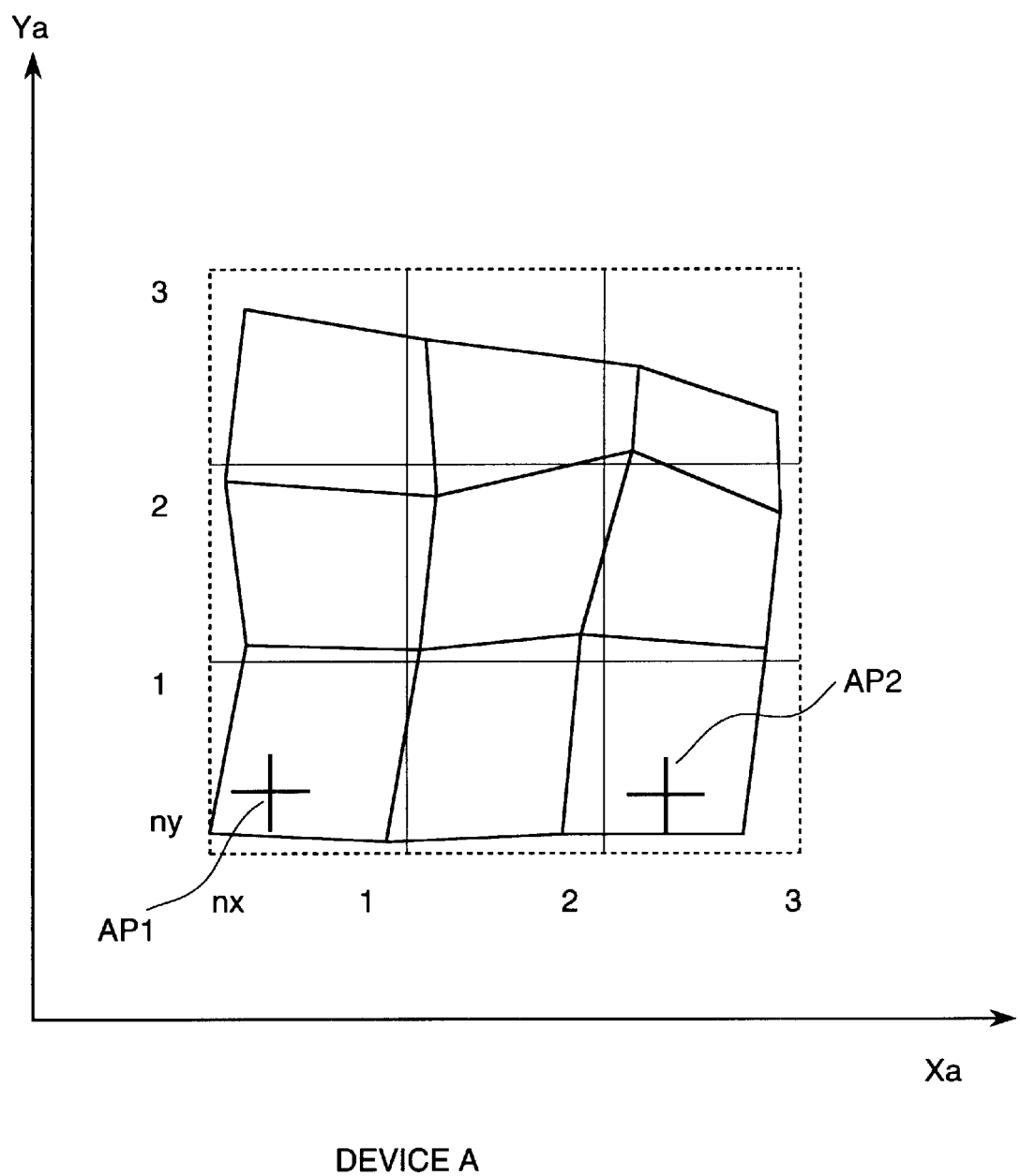
FIG. 17 is a diagram showing an example of sample stage positional accuracy.
Figure 18:
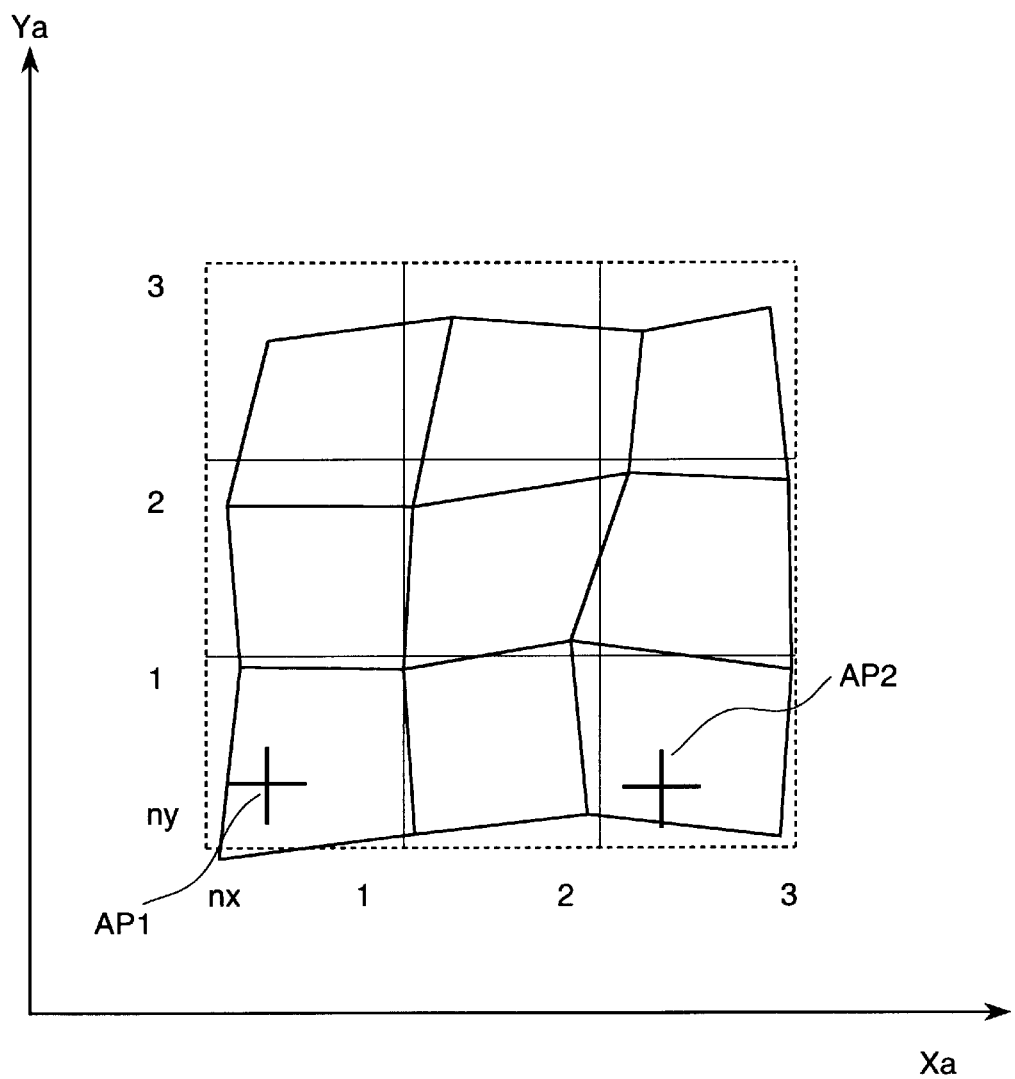
FIG. 18 is a diagram showing another example of sample stage positional accuracy.

As will be apparent from the above, even if the scanning type electron microscope device A with a stage positioning error as shown in FIG. 17 and the scanning type electron microscope device B with a stage positioning error as shown in FIG. 18 possess in common an observation sequence record, no stage positioning error because of respectively different positional deviation amount is caused.

According to the present invention as has been explained above, a visual field can be brought about with a high positional accuracy in a scanning type electron microscope. Further, the present invention is also applicable to other observation device and a microscope provided with a sample stage other than the scanning type electron microscope.

By means of the present invention, a sample stage with a high positional designation accuracy can be provided which is required for an apparatus using charged particle beam such as a scanning type electron microscope with a high observation magnification rate which is used recent semiconductor manufacturing processes for observation thereof, and further a high operation efficiency as well as a process management through an automatic observation can also be realized.

What is claimed is:

1. An apparatus using charged particle beam, which comprises a charged particle beam source for generating charged particle beams; a sample stage which holds a sample and displaces the same; a lens which converges charged particle beams emitted from the charged particle beam source onto the sample; a deflector which deflects the charged particle beams; a picture image detection means which detects a picture image of the sample; a picture image display means which displays the picture image detected; a coordinate designation means which designates a position on the sample; means for relating a coordinate value on the coordinate designation means to a coordinate value on the sample stage while permitting calibration thereof and for displacing the sample stage to a position of the sample stage corresponding to the coordinate value designated on the coordinate designation means, characterized in that the apparatus further comprising, a positional deviation amount calculation means which, when observing any observation position on the sample, displaces the sample stage so that a displacement target position designated by the coordinate designation means coincides with the observation position and calculates a positional deviation amount between a predetermined position on the sample which is detected by the picture image detection means after completing the displacement and a predetermined position of the picture image detection means; a memory means which stores the calculated positional deviation amount; and a positional deviation correction means which controls a displacement target position coordinate value used when displacing subsequently to an observation position corresponding to the previous observation position or the same observation position based on the positional deviation amount determined by the positional deviation amount calculation means and operates so that the predetermined position of the sample at the time when the sample stage stops and the predetermined position on the picture image display means coincide each other.

2. An apparatus using charged particle beam according to claim 1, further comprising an observation sequence memory unit which stores such as a planed observation position, an observation portion picture image and an observation sequence and further stores the positional deviation amount or the after-correction displacement target position coordinate value while relating to the planed observation position coordinate value.

3. An apparatus using charged particle beam according to claim 1, wherein when controlling the displacement target position coordinate at the time of displacing to an arbitrary observation position, a statistically processed result of the positional deviation amounts or the after-correction displacement target position coordinate values for a plurality of times obtained previously is used.

4. An apparatus using charged particle beam according to claim 2, wherein when controlling the displacement target position coordinate at the time of displacing to an arbitrary observation position, a statistically processed result of the positional deviation amounts or the after-correction displacement target position coordinate values for a plurality of times obtained previously is used.

5. An apparatus using charged particle beam according to claim 3, further comprising means for setting in advance an effective number of traceable past positional deviation amounts calculated by the positional deviation amount calculation means is provided.

6. An apparatus using charged particle beam according to claim 4, further comprising means for setting in advance an effective number of traceable past positional deviation amounts calculated by the positional deviation amount calculation means is provided.

7. An apparatus using charged particle beam, which comprises a charged particle beam source for generating charged particle beams; a sample stage which holds a sample and displaces the same; a lens which converges charged particle beams emitted from the charged particle beam source onto the sample; a deflector which deflects the charged particle beams; a picture image detection means which detects a picture image of the sample; a picture image display means which displays the picture image detected; a coordinate designation means which designates a position on the sample; means for relating a coordinate value on the coordinate designation means to a coordinate value on the sample stage while permitting calibration thereof and for displacing the sample stage to a position of the sample stage corresponding to the coordinate value designated on the coordinate designation means, characterized in that the apparatus further comprising, a positional deviation amount calculation means which, when observing any observation position on the sample, displaces the sample stage so that a displacement target position designated by the coordinate designation means coincides with the observation position and calculates a positional deviation amount between a predetermined position on the sample which is detected by the picture image detection means after completing the displacement and a predetermined position of the picture image detection means; means for determining after-correction displacement target position coordinate value after correcting the displacement target position coordinate value used at the moment by making use of the calculated positional deviation; a memory means which stores the determined after-correction target position coordinate value; and a positional deviation correction means which controls a displacement target position coordinate value used when displacing subsequently to an observation position corresponding to the previous observation position or the same observation position based on the after-correction displacement target position coordinate value stored in the memory means and operates so that the predetermined position of the sample at the time when the sample stage stops and the predetermined position on the picture image display means coincide each other.

8. An apparatus using charged particle beam according to claim 7, further comprising an observation sequence memory unit which stores such as a planed observation position, an observation portion picture image and an observation sequence and further stores the positional deviation amount or the after-correction displacement target position coordinate value while relating to the planed observation position coordinate value.

9. An apparatus using charged particle beam according to claim 7, wherein when controlling the displacement target position coordinate at the time of displacing to an arbitrary observation position, a statistically processed result of the positional deviation amounts or the after-correction displacement target position coordinate values for a plurality of times obtained previously is used.

10. An apparatus using charged particle beam according to claim 8, wherein when controlling the displacement target position coordinate at the time of displacing to an arbitrary observation position, a statistically processed result of the positional deviation amounts or the after-correction displacement target position coordinate values for a plurality of times obtained previously is used.

11. An apparatus using charged particle beam according to claim 9, further comprising means for setting in advance an effective number of traceable past positional deviation amounts calculated by the positional deviation amount calculation means is provided.

12. An apparatus using charged particle beam according to claim 10, further comprising means for setting in advance an effective number of traceable past positional deviation amounts calculated by the positional deviation amount calculation means is provided.

13. An apparatus using charged particle beam according to one of claims 1 through 12, further comprising a device identification means which identifies an apparatus using charged particle beam for which the positional deviation amount or the after-correction displacement target position coordinate value has been obtained, wherein the positional deviation amount memory means or the after-correction displacement target position coordinate value memory means stores the positional deviation amount or the after-correction displacement target position coordinate value for every apparatus using charged particle beam identified by the device identification means while relating to the planed observation position, and when determining the displacement target position of the sample stage by the positional deviation correction means, the displacement target position of the sample stage is determined based on the statistically processed result of the detected positional deviation amount or the after-correction displacement target position coordinate value reflected by the detected positional deviation amount.

14. An apparatus using charged particle beam according to one of claims 1 through 12, further comprising means for switching the positional deviation correction means between valid and invalid.

15. An apparatus using charged particle beam according to claim 14, further comprising means for storing the setting between valid and invalid of the positional deviation correction means while relating in advance with the observation sequence memory means and the valid and invalid of the positional deviation correction means is controlled at the time of automatic observation.

16. An apparatus using charged particle beam according to one of claims 1 through 12, further comprising means for switching the positional deviation amount calculation means between valid and invalid.

17. An apparatus using charged particle beam according to claim 16, further comprising means for storing the setting between valid and invalid of the positional deviation amount calculation means while relating in advance with the observation sequence memory means and the valid and invalid of the positional deviation amount calculation means is controlled at the time of automatic observation.

18. An apparatus using charged particle beam, which comprises; a sample stage which displaces in two dimensional direction; a coordinate value designation means which designates a position on a sample; means for relating a coordinate value on the coordinate value designation means to a coordinate value on the sample stage while permitting calibration thereof and for displacing the sample stage to a position of the sample stage corresponding to the coordinate value designated on the coordinate value designation means, characterized in that the apparatus further comprising, a target position deviation detection means for detecting in a microscope visual field a positional deviation amount between a target position designated by the coordinate value designation means and a position after displacement of the sample stage; a positional deviation amount memory means for storing the positional deviation detection result by the target position deviation detection means while relating to the target position; and a positional deviation correction means which determines a displacement target position of the sample stage based on a statistical processing result of the positional deviation detection result relating to the concerned target position stored previously in the positional deviation amount memory means when designating the target position by the coordinate value designation means and displacing the sample stage to the target position.

* * * * *